United States Patent
Nakamura et al.

(10) Patent No.: US 7,371,835 B2
(45) Date of Patent: May 13, 2008

(54) P53-DEPENDENT APOPTOSIS-INDUCING PROTEIN AND METHOD OF SCREENING FOR APOPTOSIS REGULATOR

(75) Inventors: Yusuke Nakamura, Kanagawa (JP); Hirofumi Arakawa, Tokyo (JP)

(73) Assignees: Japan as Represented by the President of the University of Tokyo, Bunkyo-ku (JP); Oncotherapy Science, Inc., Minato-ku (JP)

( * ) Notice: Subject to any disclaimer, the term of this patent is extended or adjusted under 35 U.S.C. 154(b) by 291 days.

(21) Appl. No.: 10/484,157

(22) PCT Filed: Jul. 18, 2002

(86) PCT No.: PCT/JP02/07305

§ 371 (c)(1),
(2), (4) Date: Jul. 26, 2004

(87) PCT Pub. No.: WO03/008581

PCT Pub. Date: Jan. 30, 2003

(65) Prior Publication Data

US 2004/0253595 A1    Dec. 16, 2004

(30) Foreign Application Priority Data

Jul. 19, 2001   (JP) .............................. 2001-220349

(51) Int. Cl.
C07H 21/02   (2006.01)
C07K 1/00    (2006.01)
C07K 14/00   (2006.01)
C12N 5/00    (2006.01)
C12P 21/06   (2006.01)

(52) U.S. Cl. ..................... 536/23.1; 530/350; 435/325; 435/69.1

(58) Field of Classification Search ...... None
See application file for complete search history.

(56) References Cited

U.S. PATENT DOCUMENTS 6,746,846 B1 *  6/2004  Wang et al. .................. 435/7.1
6,783,961 B1 *  8/2004  Edwards et al. ........... 435/91.1
2005/0196754 A1 *  9/2005  Drmanac et al. .............. 435/6

FOREIGN PATENT DOCUMENTS

WO   WO200231111   * 4/2002

OTHER PUBLICATIONS

Okamura et al., Mol cell vol. 8, p. 85-94, Jul. 2001.*
Arakawa, Hirofumi et al.; "The novel p53-target genes and the novelty in the mechanism of p53 tumor suppression: Identification of *p53R2* and its significance" (translation); *Experimental Medicine* (translation); 2000; pp. 2204-2211; vol. 18, No. 16 (In Japanese).
Arakawa, Hirofumi et al.; *Experimental Medicine* (translation); 2000; pp. 2340-2342; vol. 18, No. 17 (In Japanese).
Arakawa, Hirofumi et al.; *Experimental Medicine* (translation); 2001; pp. 1050-1056; vol. 19, No. 9 (In Japanese).
Bulavin, Dmitry V. et al.; "Phosphorylation of human p53 by p38 kinase coordinates N-terminal phosphorylation and apoptosis in response to UV radiation"; *The EMBO Journal*; 1999, pp. 6845-6854; vol. 18, No. 23; European Molecular Biology Organization.
El-Deiry, Wafik S. et al.; "Definition of a consensus binding site for p53"; *Nature Genetics*; Apr. 1992; pp. 45-49; vol. 1.
Giaccia, Amato J. and Michael B. Kastan; "The complexity of p53 modulation: emerging patterns from divergent signals"; *Genes & Development*; 1998; pp. 2973-2983; vol. 12; Cold Spring Harbor Laboratory Press.
Hirao, Atsushi et al.; "DNA damage-induced activation of p53 by the checkpoint kinase Chk2"; *Science*: Mar. 10, 2000; pp. 1824-1827; vol. 287.
Jeggo, P. A.; "Identification of genes involved in repair of DNA double-strand breaks in mammalian cells"; *Radiation Research*; 1998; pp. S80-S91; vol. 150 (Suppl.); Radiation Research Society.
Kimura, Yasutoshi et al.; "Genomic structure and chromosomal localization of GML (GPI-anchored molecule-like protein), a gene induced by p53"; *Genomics*; 1997; pp. 477-480; vol. 41; Academic Press.
Levine, Arnold J.; "p53, the cellular gatekeeper for growth and division"; *Cell*; Feb. 7, 1997; pp. 323-331; vol. 88; Cell Press.
Miyashita, Toshiyuki and John C. Reed; "Tumor suppressor p53 is a direct transcriptional activator of the human *bax* gene"; *Cell*; Jan. 27, 1995; pp. 293-299; vol. 80; Cell Press.

(Continued)

*Primary Examiner*—Larry R. Helms
*Assistant Examiner*—Lei Yao
(74) *Attorney, Agent, or Firm*—Townsend and Townsend and Crew LLP

(57) ABSTRACT p53-dependent Damage-Inducible Nuclear Protein 1 (p53DINP1 protein) is a p53-induced nuclear protein that induces p53-dependent apoptosis by regulating p53 function through Ser 46 phosphorylation. A DNA encoding p53DINP1 can be applied as anticancer agents for destroying neoplasms such as tumors, and as therapeutic or preventive agents for diseases associated with p53-mediated apoptosis abnormalities. It is also possible to apply the above protein and DNA in methods of screening for candidate compounds for regulating p53-mediated apoptosis.

4 Claims, 10 Drawing Sheets

OTHER PUBLICATIONS

Momand, Jamil et al.; "The *mdm-2*oncogene product forms a complex with the p53 protein and inhibits p53-mediated transactivation"; *Cell*; Jun. 26, 1992; pp. 1237-1245; vol. 69; Cell Press.

Oda, Katsutoshi et al.; "*p53AIP1*, a potential mediator of p53-dependent apoptosis, and its regulation by Ser-46-phosphorylated p53"; *Cell*; Sep. 15, 2000; pp. 849-862; vol. 102; Cell Press.

Okamura, Shu et al.; "*p53DINP1*, a p53-inducible gene, regulates p53-dependent apoptosis"; *Molecular Cell*; Jul. 2001; pp. 85-94; vol. 8; Cell Press.

Oliner, J. D. et al.; "Amplification of a gene encoding a p53-associated protein in human sarcomas"; *Nature*; Jul. 2, 1992; pp. 80-83; vol. 358.

Payne, Gillian et al.; "Kinetics of p56$^{lck}$ and p60$^{src}$ Src homology 2 domain binding to tyrosine-phosphorylated peptides determined by a competition assay or surface plasmon resonance"; *Proc. Natl. Acad. Sci. U.S.A.*; Jun. 1993; pp. 4902-4906; vol. 90.

Prives, Carol; "Signaling to p53: breaking the MDM2-p53 circuit"; *Cell*; Oct. 2, 1998; pp. 5-8; vol. 95; Cell Press.

Sarkaria, Jann et al.; "Inhibition of ATM and ATR kinase activities by the radiosensitizing agent, caffeine"; *Cancer Research*; Sep. 1, 1999; pp. 4375-4382; vol. 59.

Shieh, Sheau-Yann et al.; "DNA damage-induced phosphorylation of p53 alleviates inhibition by MDM2"; *Cell*; Oct. 31, 1997; pp. 325-334; vol. 91; Cell Press.

Shieh, Sheau-Yann et al.; "DNA damage-inducible phosphorylation of p53 at N-terminal sites including a novel site, Ser20, requires tetramerization"; *The EMBO Journal*; 1999; pp. 1815-1823; vol. 18, No. 7; European Molecular Biology Organization.

* cited by examiner

```
                    Amended
p53DINP1a (SEQ ID NO:2) 1  MFQRLNKMFVGEVSSSSNQEPEFNEKEDDE  30
p53DINP1b (SEQ ID NO:4) 1  MFQRLNKMFVGEVSSSSNQEPEFNEKEDDE  30

1a  31  WILVDFIDTCTGFSAEEEEEEEDISEESPT   60
            1b  31  WILVDFIDTCTGFSAEEEEEEEDISEESPT   60

1a  61  EHPSVFSCLPASLECLADTSDSCFLQFESC   90
            1b  61  EHPSVFSCLPASLECLADTSDSCFLQFESC   90

1a  91  PMEESWFITPPPCFTAGGLTTIKVETSPME  120
            1b  91  PMEESWFITPPPCFTAGGLTTIKVETSPME  120

1a 121  NLLIEHPSMSVYAVHNSCPGLSEATRGTDE  150
            1b 121  NLLIEHPSMSVYAVHNSCPGLSEATRGTDE  150

1a 151  LHSPSSPRVEAQNEMGQHIHCYVAALAAHT  180
            1b 151  LHSPSSPRARKSCL*                 164

1a 181  TFLEQPKSFRPSQWIKEHSERQPLNRNSLR  210

1a 211  RQNLTRDCHPRQVKHNGWVVHQPCPRQYNY* 240
```

B

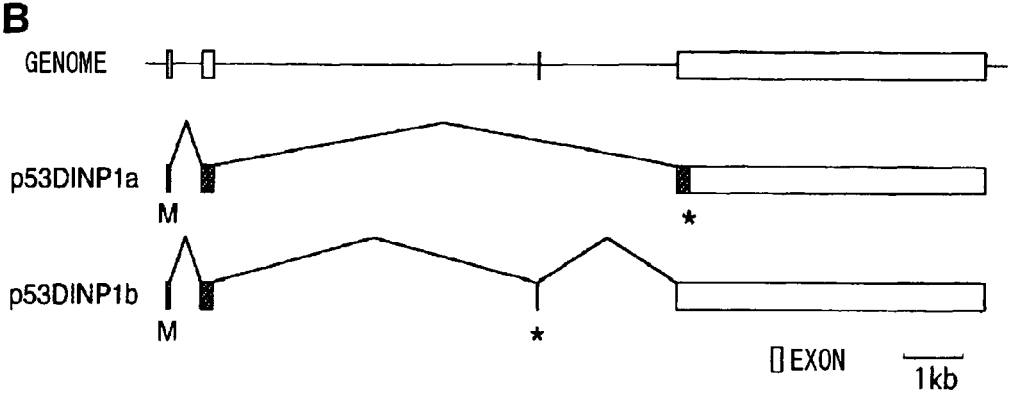

FIG. 9
A
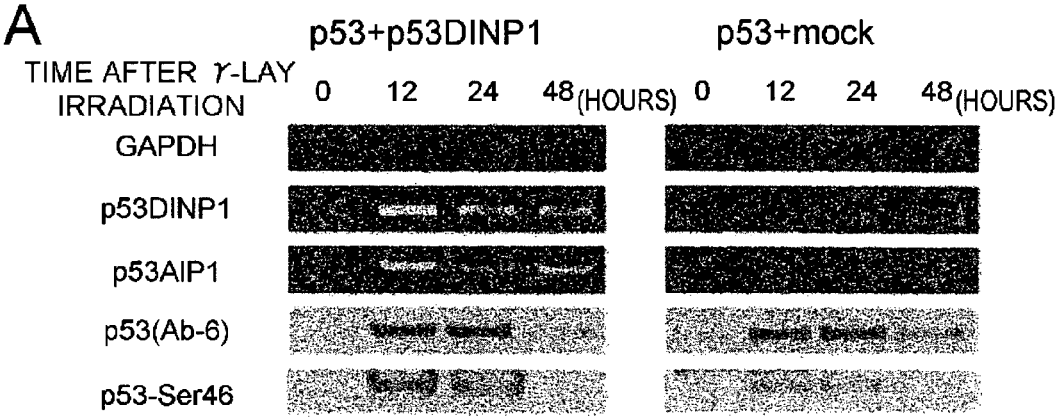
B
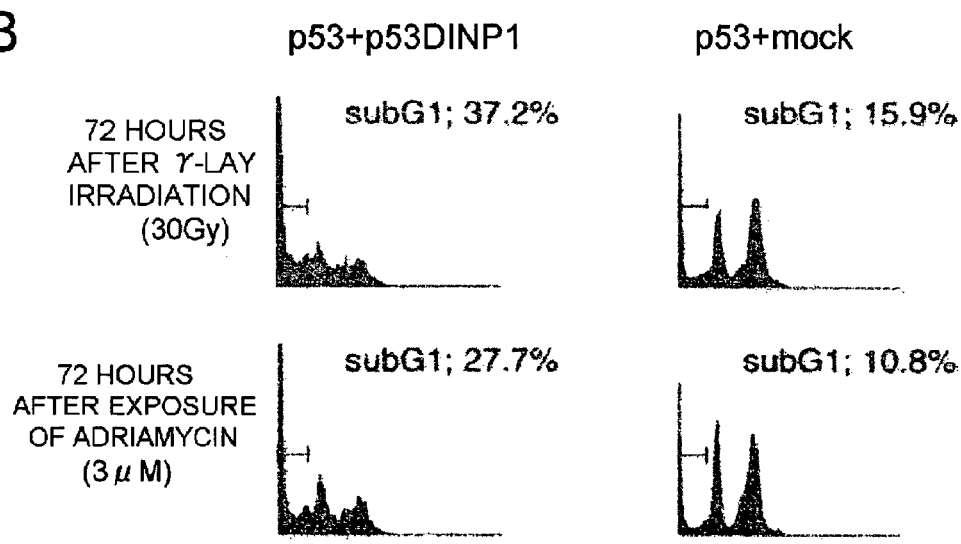
C

ically, mediated by p21^{Waf1} and BAX respectively. These functions were thought to be characteristics essential for p53-dependent tumor suppression (el-Deiry, W. S., Tokino, T., Velculescu, V. E., Levy, D. B., Parsons, R., Trent, J. M., Lin, D., Mercer, W. E., Kinzler, K. W., and Vogelstein, B. (1993). WAF1, a potential mediator of p53 tumor suppression. Cell 75, 817-825; Harper, J. W., Adami, G. R., Wei, N., Keyomarsi, K., and Elledge, S. J. (1993). The p21 Cdk-interacting protein Cip1 is a potent inhibitor of G1 cyclin-dependent kinases. Cell 75, 805-816; Miyashita, T. and Reed, J. C. (1995). Tumor suppressor p53 is a direct transcriptional activator of the human bax gene. Cell 80, 293-299).
P53-DEPENDENT APOPTOSIS-INDUCING PROTEIN AND METHOD OF SCREENING FOR APOPTOSIS REGULATOR

TECHNICAL FIELD

The present invention relates to a novel p53-dependent apoptosis-inducing protein, a gene that encodes the protein, and such. It also relates to a method of screening for compounds capable of regulating p53-dependent apoptosis.

BACKGROUND ART

Of the genes known to be involved in human cancer, mutations have been most commonly detected in the tumor suppressor gene p53. The p53 gene product activates transcription of many downstream genes, and by regulating their transcription, exerts a variety of biological functions. The two main functions of p53 are cell cycle arrest and apoptosis, mediated by p21$^{Waf1}$ and BAX respectively. These functions were thought to be characteristics essential for p53-dependent tumor suppression (el-Deiry, W. S., Tokino, T., Velculescu, V. E., Levy, D. B., Parsons, R., Trent, J. M., Lin, D., Mercer, W. E., Kinzler, K. W., and Vogelstein, B. (1993). WAF1, a potential mediator of p53 tumor suppression. Cell 75, 817-825; Harper, J. W., Adami, G. R., Wei, N., Keyomarsi, K., and Elledge, S. J. (1993). The p21 Cdk-interacting protein Cip1 is a potent inhibitor of G1 cyclin-dependent kinases. Cell 75, 805-816; Miyashita, T. and Reed, J. C. (1995). Tumor suppressor p53 is a direct transcriptional activator of the human bax gene. Cell 80, 293-299).

The present inventors recently discovered p53R2, a novel p53 target molecule that supplies deoxyribonucleotides for DNA repair. Thus, p53 is also directly involved in DNA repair (Tanaka, H., Arakawa, H., Yamaguchi, T., Shiraishi, K., Fukuda, S., Matsui, K., Takei, Y., and Nakamura, Y. (2000). A ribonucleotide reductase gene involved in a p53-dependent cell-cycle checkpoint for DNA damage. Nature 404, 42-49).

To date, it has been reported that a large number of p53 target genes, and approximately one hundred candidates for p53-binding sequences, are present in human chromosomes. It is thought the bioactivity of this vast number of p53 target genes is reflected in p53's tumor suppressing actions resulting from by p53-mediated cell cycle arrest, DNA repair and apoptosis. Therefore, identifying additional p53 target genes is important in elucidating the mechanisms of tumorigenesis, and cell protection from genotoxic stresses.

Induction of apoptosis is known to be the most important of p53's tumor suppressing functions, and this activity is being used to kill cancer cells in human patients (Levine, Cell: 88, 323-331, 1997). However, despite this kind of evidence, the mechanism of p53-mediated apoptosis has yet to be elucidated.

BAX, Fas, Killer/DR5, and PIGs are recognized as candidates for mediating p53-dependent apoptosis, and their functions are currently being investigated. However, acting alone, any one of these candidates is insufficient to induce apoptosis. The current inventors have found p53AIP1, a novel target gene for p53, which differs from the candidates described above in that it can induce apoptosis independently when over-expressed in some cancer cells. Blocking p53AIP1 expression inhibits p53-mediated apoptosis (Oda, K., Arakawa, H., Tanaka, T., Matsuda, K., Tanikawa, C., Mori, T., Nishimori, H., Tamai, K., Tokino, T., Nakamura, Y., and Taya, Y. (2000) p53AIP1, a potential mediator of p53-dependent apoptosis, and its regulation by Ser-46-phosphorylated p53. Cell 102, 849-862) These results suggested that p53AIP1 was a crucial mediator in the mechanism of p53-dependent apoptosis.

Growing evidence suggests that the biological activity of p53 is determined by modifications such as phosphorylation, acetylation, and the like (Giaccia, A. J. and Kastan, M. B. (1998). The complexity of p53 modulation: emerging patterns from divergent signals. Genes Dev. 19, 2973-2983). For example, there are reports indicating that phosphorylation of the p53 protein at its Ser15 and Ser20 residues is important in p53 activation in response to DNA damage (Shieh, S. Y., Ikeda, M., Taya, Y., and Prives, C. (1997) DNA damage-induced phosphorylation of p53 alleviates inhibition by MDM2. Cell 91, 325-334; Shieh, S. Y., Taya, Y., and Prives, C. (1999) DNA damage-inducible phosphorylation of p53 at N-terminal sites including a novel site, Ser20, requires tetramerization. EMBO J. 18, 1815-1823). There are also reports that acetylation of the p53 C-terminal domain enhances DNA binding activity (Gu, W. and Roeder, R. G. (1997). Activation of p53 sequence-specific DNA binding by acetylation of the p53 C-terminal domain. Cell 90, 595-606). In addition, ATM and CHK2 proteins have been proposed as strong candidates for a kinase involved in the phosphorylation of p53 at Ser15 and Ser20 respectively (Sarkaria, J. N., Busby, E. C., Tibbetts, R. S., Roos, P., Taya, Y., Karnitz, L. M, and Abraham, R. T. (1999). Inhibition of ATM and ATR kinase activities by the radiosensitizing agent, caffeine. Cancer Res. 59, 4375-4382; Hirao, A., Kong, Y. Y., Matsuoka, S., Wakeham, A., Ruland, J., Yoshida, H., Liu, D., Elledge, S. J., and Mak, T. W. (2000). DNA damage-induced activation of p53 by the checkpoint kinase Chk2. Science 287, 1824-1827). Furthermore, it has been shown that phosphorylation of the Ser46 residue is essential for p53-induced apoptosis (Oda et al., supra).

Based on the various findings described above, the present inventors speculated that p53 determines whether cells with damaged DNA will survive or be killed, such that cells which are extremely damaged or have been exposed to danger are eliminated through phosphorylation of p53 at Ser46, and induction of p53AIP1.

Because known p53 targets do not sufficiently explain this speculation, the present inventors used a method capable of directly cloning human chromosome-derived p53-binding sequences for further screening of p53 targets. The present inventors identified four novel target genes and a GPI-anchored molecule-like protein (GML), whose expressions are induced by wild-type p53 (Furuhata, T., Tokino, T., Urano, T., and Nakamura, Y. (1996). Isolation of a novel GPI-anchored gene specifically regulated by p53; correlation between its expression and anti-cancer drug sensitivity. Oncogene 13, 1965-1970; Kimura, Y., Furuhata, T., Urano, T., Hirata, K., Nakamura, Y., and Tokino, T. (1997). Genoa structure and chromosomal localization of GML (GPI-anchored molecule-like protein), a gene induced by p53. Genomics 41, 477-480), P2XM (Urano, T., Nishimori,. H., Han, H., Furuhata, T., Kimura, Y., Nakamura, Y., and Tokino, T. (1997). Cloning of P2XM, a novel human P2X receptor gene regulated by p53. Cancer Res. 57, 3281-3287), BAI1 (Nishimori, H., Shiratsuchi, T., Urano, T., Kimura, Y., Kiyono, K., Tatsumi, K., Yoshida, S., Ono, M., Kuwano, M., Nakamura, Y., and Tokino, T. (1997). A novel brain-specific p53-target gene, BAI1, containing thrombospondin type 1 repeats inhibits experimental angiogenesis. Oncogene 15, 2145-2150) and CSR (Han, H. J., Tokino, T., and Nakamura, Y. (1998). CSR, a scavenger receptor-like protein with a protective role against cellular damage caused by UV irradiation and oxidative stress. Hum. Mol. Genet. 7, 1039-1046).

The present inventors isolated a p53-inducible transcript by establishing a cell line in which p53 expression is regulated under set conditions, and then applied differential display techniques to that cell line (Takei, Y., Ishikawa, S., Tokino, T., Muto, T., and Nakamura, Y. (1998). Isolation of a novel TP53 target gene from a colon cancer cell line carrying a highly-regulated wild-type TP53 expression system. Genes Chromosomes Cancer 23, 1-9) Using this approach, three additional novel p53 target genes were identified: TP53TG1 (Takei et al., supra), TP53TG3 (Ng, C. C., Koyama, K., Okamura, S., Kondoh, H., Takei, Y., and Nakamura, Y. (1999). Isolation and characterization of a novel TP53-inducible gene, TP53TG3. Genes Chromosomes Cancer 26, 329-335) and p53R2 (Tanaka, H., Arakawa, H., Yamaguchi, T., Shiraishi, K., Fukuda, S., Matsui, K., Takei, Y., and Nakamura, Y. (2000). A ribonucleotide reductase gene involved in p53-dependent cell-cycle checkpoint for DNA damage. Nature 404, 42-49). Genes already known to be activated or suppressed by p53 were also identified during this approach.

DISCLOSURE OF THE INVENTION

Although novel p53 target genes have been identified one after another, many of the genes involved in p53-induced apoptosis have yet to be identified. Among the many functions of p53, target genes which can prompt cells to apoptosis have yet to be elucidated. These p53 target genes are extremely significant because they are useful for 1) actively inducing cancer cell apoptosis, and 2) elucidating the mechanism by which p53 determines whether to kill cells or to let them live.

Therefore, an objective of the present invention is to provide a novel protein that induces p53-mediated apoptosis, and a gene encoding that protein. The present invention also provides a novel method of screening for a compound that regulates apoptosis.

To achieve the above-described objectives, the present inventors conducted exhaustive studies, and as a result, identified the p53-dependent Damage-Inducible Nuclear Protein 1 (the p53DINP1 protein). The p53DINP1 protein is a p53-induced nuclear protein that induces p53-dependent apoptosis by regulating p53 function through Ser 46 phosphorylation. A cDNA and a genomic DNA encoding p53DINP1 were also identified. The present inventors also developed an antisense oligonucleotide to p53DINP1, which regulates apoptosis, and a method of screening for a compound that regulates apoptosis, and such.

More specifically, the present invention relates to:

[1] an isolated DNA of the following (a) or (b):

(a) a DNA encoding a protein comprising the amino acid sequence of SEQ ID NOs: 2 or 4, or (b) a DNA comprising the coding region of a nucleotide sequence of any one of SEQ ID NOs: 1, 3, and 5;

[2] an isolated DNA of the following (a) or (b) encoding a protein having the activity to induce apoptosis:

(a) a DNA encoding a protein comprising the amino acid sequence of SEQ ID NOs: 2 or 4, wherein one or more amino acids are substituted, deleted, inserted, and/or added, or (b) a DNA hybridizing under stringent conditions to a DNA comprising the nucleotide sequence of any one of SEQ ID NOs: 1, 3, and 5;

[3] a DNA containing at least 15 nucleotides, wherein said DNA is complementary to a DNA comprising a nucleotide sequence of any one of SEQ ID NOs: 1, 3, and 5, or to the complementary strand thereof;

[4] an isolated protein encoded by the DNA of [1] or [2];

[5] a vector comprising the DNA of [1] or [2];

[6] a host cell carrying the DNA of [1] or [2], or the vector of [5];

[7] a method for producing the protein of [4], wherein said method comprises the steps of culturing the host cell of [6], and recovering the protein expressed by said host cell;

[8] an antibody binding to the protein of [4];

[9] an antisense polynucleotide to the DNA comprising a nucleotide sequence of any one of SEQ ID NOs: 1, 3, and 5;

[10] a method of screening for a candidate compound for an apoptosis-regulating agent, wherein said method comprises the steps of:

(a) contacting a test sample with the protein of [4], (b) detecting the binding activity of the test sample to said protein, and (c) selecting a compound having the activity to bind to said protein;

[11] a method of screening for a candidate compound for an apoptosis-regulating agent, wherein said method comprises the steps of:

(a) contacting a test sample with the protein of [4] in the presence of p53, (b) measuring the phosphorylation level of said p53 protein at the Ser46 residue after the contact, and (c) selecting a compound capable of regulating apoptosis based on the phosphorylation level measured in step (b);

[12] a method of screening for a candidate compound for an apoptosis-regulating agent, wherein said method comprises the steps of:

(a) contacting a test sample with a cell containing a vector having the structure in which the p53-binding sequence of SEQ ID No: 8 and a reporter gene are operably linked, or an extract of said cell, (b) measuring the expression level of said reporter gene, and (c) selecting a compound capable of decreasing or increasing the expression level of said reporter gene measured in step (b), compared to that measured in the absence of the test sample; and

[13] an apoptosis-regulating agent comprising as an effective ingredient a compound selected by a method of any one of [10] to [12].

The present invention is described in detail below.

The present invention relates to a novel protein p53DINP1, whose expression is induced by p53. p53DINP1 is involved in the phosphorylation of p53 at the Ser46 residue during p53-induced apoptosis caused by DNA damage such as double-strand breaks. P53DINP1 also enhances expression of the p53-dependent apoptosis protein, p53AIP1.

Preferred examples of such a protein include "p53DINP1a" and "p53DINP1b", comprising amino acid sequences shown in SEQ ID NOs: 2 and 4 respectively (unless otherwise stated, "p53DINP1a" and "p53DINP1b" proteins are hereinafter collectively described as "p53DINP1" proteins). The present invention also includes proteins analogous to "p53DINP1" proteins, as long as their physiological activity is the same as described above. Such analogous proteins include mutant "p53DINP1" proteins produced artificially, or isolated from humans or other organisms, and having amino acid sequences with one or more amino acid substitutions, deletions, insertions, and/or additions compared with those shown in SEQ ID NOs: 2 or 4. Such analogous proteins also include proteins encoded by DNAs that hybridize to the cDNAs that encode p53DINP1.

As used herein, "isolated" refers to material (for example, a polynucleotide or a polypeptide) which has been extracted from its original environment (for example, the natural environment if it occurs naturally), and which has been altered "by means of human intervention". "Isolated" also refers to material present in a sample and substantially rich in a compound of interest, and/or material present in a sample containing the compound of interest in a partially or substantially purified form. As used herein, the term "substantially purified" refers to a compound that has been separated from its natural environment and is at least 60% or more, preferably 75% or more, and most preferably 90% or more free of other components with which the compound naturally occurs.

With regards to "amino acid sequences with one or more amino acid substitutions, deletions, insertions, and/or additions", the number or position of amino acid mutations is not limited, as long as mutants maintain p53DINP1 protein functions. The proportion of mutations in the protein is typically 10% or less, preferably 5% or less, and most preferably 1% or less of total amino acids.

The "p53DINP1" proteins can be prepared by extraction from the tissues of mammals, for example, of primates such as humans or rodents such as mice, using an anti-p53DINP1 antibody as described below, or the like. All human cells express p53DINP1 proteins, so the type of tissue is not limited as long as human tissue is used. The thymus, pancreas, spleen, testis, and peripheral leukocytes express large amounts of p53DINP1 protein and are thus suitable for use. A transformant comprising a vector carrying a DNA that encodes p53DINP1 can be conveniently used for p53DINP1 purification, as described below.

Proteins analogous to the above described p53DINP1 proteins can be prepared using a hybridization technique known to those skilled in the art. For example, by using a nucleotide sequence encoding p53DINP1 (for example, a nucleotide sequence from SEQ ID NOs: 1, 3, or 5) or a portion thereof as a probe, proteins analogous to the p53DINP1 proteins can be obtained by isolating, from a variety of mammals including humans and other organisms, DNAs highly homologous to p53DINP1 cDNA. DNAs highly homologous to p53DINP1 cDNA can also be prepared by PCR (polymerase chain reaction) using as a primer the nucleotide sequence shown in SEQ ID NOs: 1, 3, or 5, or a portion thereof. PCR is known to those skilled in the art.

Those skilled in the art can select stringent hybridization conditions appropriate for isolating DNAs encoding polypeptides functionally equivalent to the p53DINP1 polypeptides. For example, pre-hybridization is carried out in a hybridization solution containing 25% formamide (50% formamide under more stringent conditions), 4×SSC, 50 mM Hepes (pH 7.0), 10×Denhardt's solution, and 20 µg/ml denatured salmon sperm DNA at 42° C. overnight. A labeled probe is added and hybridization is carried out by incubation at 42° C. overnight. Post-hybridization washes are carried out under different levels of stringency including moderately stringent "1×SSC, 0.1% SDS, 37° C.", highly stringent "0.5×SSC, 0.1% SDS, 42° C.", and more highly stringent "0.2×SSC, 0.1% SDS, 65° C." conditions. As the stringency level of post-hybridization washes increases, DNA more highly homologous to the probe sequence is expected to be isolated. The above-described combinations of SSC, SDS, and temperature are merely examples of wash conditions. Those skilled in the art can achieve the same stringencies as those described above by appropriately combining the above factors or others (such as probe concentration, probe length, hybridization period, etc.) that affect hybridization stringency.

A polypeptide thus isolated using hybridization will usually comprise an amino acid sequence highly homologous to the polypeptides identified by the present inventors. "Highly homologous" refers to sequence homology of at least 40% or more, preferably 60% or more, further preferably 80% or more, further preferably 90% or more, further preferably at least 95% or more, further preferably at least 97% or more (for example, 98% to 99%). Amino acid sequence identity can be determined, for example, using the BLAST algorithm according to Karlin and Altschul (Proc. Natl. Acad. Sci. USA. 87:2264-2268, 1990; Proc. Natl. Acad. Sci. USA. 90: 5873-5877, 1993). A program designated BLASTX has been developed based on this algorithm (Altschul et al., J. Mol. Biol. 215: 403-410, 1990). For analysis of amino acid sequence identity, the BLASTX program uses, for example, a score of 50 and a word length of 3 as parameters. The default parameters of the BLAST and the Gapped BLAST programs respectively are used. Specific methodology for performing BLAST analyses is publicly available on the World Wide Web at ncbi.nlm.nih.gov.

Proteins structurally analogous to p53DINP1 can be prepared not only from naturally occurring proteins, but also by artificially modifying p53DINP1 proteins comprising a sequence shown in SEQ ID NO: 2 or 4. This kind of artificial modification of DNAs coding for p53DINP1 proteins, for example the DNA of SEQ ID NO: 1, 3, or 5, can be undertaken by those skilled in the art using known methods, including PCR, cassette mutagenesis, or site-directed mutagenesis using deletion-mutants.

To ascertain whether the p53DINP1-analogous proteins thus obtained comprise activities similar to p53DINP1, such as participation in p53 Ser46 phosphorylation and induction of p53AIP1 expression, Western blot analysis using antibodies specific to phosphorylated p53 Ser46 and p53AIP1 respectively, can be used.

The p53DINP1 proteins and their above-described analogous proteins induce apoptosis-related p53AIP1 expression, and also enhance p53 Ser46 phosphorylation, a process involved in the initial signal of the p53-induced apoptosis pathway. Thus these proteins are effective as pharmaceutical agents capable of inducing apoptosis of neoplasms such as tumors that are unfavorable to organisms. They can also be used for the production of antibodies against p53DINP1 proteins and such. To produce such antibodies, it is not always necessary to use the entire sequence of a protein comprising an above-mentioned activity. A portion of the protein can also be used.

The DNAs encoding the "p53DINP1" proteins of the present invention also include cDNA, genomic DNA and synthetic DNA, as long as the DNA encodes 1) a protein having the function of inducing p53 phosphorylation at the Ser46 residue after a double stranded-DNA break or the like, and/or 2) a protein comprising the activity of inducing p53AIP1 expression.

Preferable cDNAs that encode "p53DINP1" proteins comprise, for example, the sequence of SEQ ID NO: 1 or 3, but are not limited thereto. Favorable cDNAs also include those comprising the same function as p53DINP1 cDNA. Such cDNAs can be selected from a cDNA library derived from a tissue of an organism expressing a protein comprising an above-mentioned activity. This can be achieved by hybridization using a labeled DNA probe comprising the sequence of SEQ ID NO: 1 or 3, or a portion thereof. The above cDNAs can also be prepared by RT-PCR, using as a template, total RNA derived from a tissue of an organism that expresses a protein comprising an above-mentioned activity, and using as a primer a synthetic oligonucleotide that includes a portion of SEQ ID NO: 1 or 3.

One example of the preferred genomic DNAs encoding the p53DINP1 proteins comprises the sequence of SEQ ID NO: 5. Since this genomic DNA is mapped to human chromosome 8q22, it can be isolated from a genomic DNA library prepared using chromosomal DNA containing the 8q22 region. In addition to DNA comprising the sequence of SEQ ID NO: 5, genomic DNA encoding a protein comprising the above activity can also be isolated using the above tissue-derived genomic DNA library previously used for isolation of the above cDNA.

The above-described DNAs can also be synthesized using a commercially available DNA synthesizer. For example, DNAs having the sequence of SEQ ID NOs: 1, 3, or 5, or complementary strands thereof are synthesized, and these DNAs are annealed to prepare desired double stranded DNAs.

The above-mentioned DNAs encoding "p53DINP1" proteins, and in particular the cDNAs, are useful in the production of proteins comprising the activity of inducing p53 Ser46 phosphorylation, and the like. When used to produce such proteins, the DNAs are preferably inserted into an appropriate expression vector.

An appropriate expression vector can be suitably selected in accordance with the translation system used for protein production. A cellular or cell-free translation system can be selected, depending on the purpose. In a cellular translation system, vectors that can be used for expression in *Escherichia coli* include pkk223-3, pkk233-2, and pJLA502. A protein of the present invention can also be expressed as a fusion protein with other proteins. Vectors for fusion protein expression are exemplified by pRIT2T, pGEX-2T, pGEX-3X, and such. Fusion proteins are easily recovered using an affinity column. The use of a vector comprising a thrombin- or factor Xa-cleavage site at the connecting site of the fusion partners enables specific recovery of the target protein. Examples of vectors for secretion of proteins into the periplasm or outside of cells include pKT280 and pRIT5 (Okada, M. and Miyazaki, K., ed. Formidable Biotechnical Series. Protein Experimental Note, I, Extraction and Separation/Purification, Yodosha, 1996, pp. 139-149). The proteins of this invention may also be expressed in insect and mammalian cells using baculoviruses. An example of a baculovirus vector for use in mammalian cells is pAcCAG-MCS1 (Muramatsu, M., ed. Laboratory Manual for Gene Technology, 3$^{rd}$ ed., Maruzen, 1996, pp. 242-246).

Recombinant proteins expressed in host cells can be purified by a method well known in the art. When a protein of this invention is expressed in the form of a fusion protein linked at the N-terminus to a histidine residue tag, glutathione-S-transferase (GST), or such, it can be purified through a nickel column, glutathione Sepharose column, etc.

DNAs encoding "p53DINP1" proteins of the present invention may be applied in gene therapy of disorders caused by their mutation or deletion. They may also be useful for apoptosis induction in unfavorable neoplasms such as tumors. When applied as above, it is preferable to insert the DNA into a vector to deliver that DNA into the desired tissue or cell. Examples of a vector used for gene therapy include viral vectors such as retroviral vectors, adenoviral vectors, adeno-associated viral vectors, vaccinia virus vectors, lentivirus vectors, herpes virus vectors, alphavirus vectors, EB virus vectors, papillomavirus vectors, and foamy virus vectors; and non-viral vectors such as cationic liposomes, ligand DNA complexes, gene guns (Y. Niitsu et al., Molecular Medicine 35, 1385-1395, 1998), and such. Gene transduction may be carried out in vivo, ex vivo, etc.

The above-described DNA can be used as a full length DNA, or as a portion thereof, in hybridization probes, PCR primers, or ribozyme derivatives. Fragment length is preferably enough to ensure probe specificity and such, for example, a length of at least 15 nucleotides. Examples of such polynucleotides are those that specifically hybridize to DNAs that comprise the nucleotide sequence of SEQ ID NO: 1, 3, or 5, or to a complementary strand thereof. As used herein, the phrase "specifically hybridize" means that no significant cross-hybridization to DNAs encoding other proteins occurs during hybridization. When applied to cloning of the DNAs encoding the proteins of the present invention, or to restriction fragment length polymorphism (RFLP) analysis and such, the above-mentioned probes and primers can be used to detect polymorphisms or mutations in genes or cDNAs.

In addition to p53, p53-binding sequences included in the DNA of SEQ ID NO: 1, 3, or 5, for example, partial sequences containing the sequence of SEQ ID NO: 8, can be used to regulate transcription by binding to p53 and hence regulating expression of an operably-linked downstream gene.

The present invention also relates to antisense polynucleotides of DNAs that encode the proteins of this invention. The antisense polynucleotides of this invention suppress expression of the proteins of the present invention, and are hence useful in developing reagents for elucidating the mechanisms of disorders associated with p53-dependent apoptosis, and in developing drugs for the treatment of these disorders. Examples of such antisense polynucleotides are those having the sequences of SEQ ID NOs: 15 and 16. In addition, the antisense polynucleotides comprise those that hybridize to a nucleotide sequence of SEQ ID NO: 1 or 3, or to a nucleotide sequence within the coding region of SEQ ID NO: 5. Furthermore, the antisense polynucleotides need not be completely complementary to the nucleotide sequence of SEQ ID NO: 1 or 3, or to the nucleotide sequence within the coding region of SEQ ID NO: 5, as long as they are capable of effectively inhibiting the expression of the proteins of the present invention.

The present invention also relates to antibodies binding to the proteins of this invention. The antibodies of this invention include both polyclonal and monoclonal antibodies, as long as they can bind specifically to the proteins of this invention. The polyclonal antibodies are prepared according to the well-known method in which animals such as rabbits and guinea pigs are immunized with a protein of this invention, or a partial peptide thereof, the elevation of antibody titer is confirmed, and peripheral blood from the immunized animals is collected to obtain the antiserum. Monoclonal antibodies can be prepared according to a well known method in which animals such as mice are immunized with a protein of this invention or a partial peptide thereof, the elevation of antibody titer is confirmed, and the spleen (or lymph nodes) is collected from the immunized animals. Antibody-producing cells from the spleen or lymph nodes are then fused with myeloma cells to prepare hybridomas. Monoclonal antibodies can be prepared from the culture supernatant of the hybridoma producing those antibodies.

These antibodies can be used to detect expression levels and such of the proteins of this invention, and thus can be used for affinity purification of the proteins of this invention. They can also be used for testing and diagnosing disorders in test subjects, where these disorders are caused by an abnormality in expression or structure of a protein of this invention. For patients introduced with a DNA of this invention for the purposes of gene therapy and the like, expression of a protein of the present invention from the introduced DNA can be also monitored using these antibodies. The antibodies can also be used as a means of obtaining, by immunoprecipitation, a factor that interacts with a protein of this invention. In particular, the antibodies of this invention can be used to obtain a kinase that catalyses phosphorylation of p53 at the Ser46 residue, a process expected to signal p53-dependent apoptosis induction, since the proteins of this invention interact with this kinase. Methods such as ELISA and Western blotting can also be used as required for the detection of a protein of this invention.

The present invention also relates to methods of screening for candidate compounds for an apoptosis-regulating agent. The first screening method comprises the steps of: (a) contacting a test sample with a protein of this invention; (b) detecting the binding activity of the test sample to the protein or partial peptide thereof; and (c) selecting a compound comprising binding activity.

To give a specific example, a compound binding to a protein of the present invention is first screened by contacting with a test sample (for example, a culture supernatant or cell extract) expected to contain a compound capable of binding to the protein. An antibody of this invention is added, and the compound is then immunoprecipitated along with the protein of this invention. The binding of the candidate compound to the protein of this invention can be detected based, for example, on mobility shift during electrophoresis of the immunoprecipitated products. In addition, recovery of the candidate compound from a sample in which binding is detected can be carried out by using the binding activity to the protein of this invention, for example, by using affinity chromatography.

Screening may also be carried out using "West Western blotting" which comprises the steps of: (a) using a phage vector to prepare a cDNA library from tissues or cells that presumably express a protein that binds to a protein of this invention, (b) expressing the cDNA library on agarose, (c) transferring the protein onto a membrane, and (d) reacting it with the labeled protein of this invention to detect plaques that express the binding protein. Systems such as the "two-hybrid system" may also be used. In the "two-hybrid system", expression of a reporter gene in which a GAL4 DNA binding region and GAL4 transcription activation region are linked downstream a promoter comprising a binding sequence of a protein of this invention, is used to detect binding between the test protein and the protein of this invention.

Furthermore, methods well-known to those skilled in the art include 1) a method of screening for binding molecules by immobilizing a protein of the present invention on a solid phase or the like, and then reacting it with synthetic compounds, natural product banks, or random phage peptide display libraries, and 2) a method for isolating candidate compounds by high throughput screening using combinatorial chemistry.

Alternatively, since the proteins of this invention have the activities of inducing p53AIP1 expression and p53 Ser46 phosphorylation, candidate compounds that bind to the proteins of this invention can be screened and selected based on changes in these activities due to binding with the candidate compound. More specifically, a candidate compound, whose binding activity has been detected by a variety of methods as described above, can be also selected based on its effect (promotion or inhibition) on the activity of a protein of this invention. For example, p53 Ser46 phosphorylation can be measured by contacting candidate compounds with a protein of the present invention in the presence of p53, then using Western blotting, ELISA or such using an antibody that specifically recognizes the phosphorylated p53 protein at the Ser46 residue.

Examples of test samples for this screening include, but are not limited to, cell extracts, gene library expression products, synthetic low molecular weight compounds, proteins, natural or synthetic peptides, natural compounds, and sera. A compound that are isolated by the above-described screening, i.e., a screening using as an index the binding activity to a protein of this invention, may also be used as a test samples.

A protein of this invention comprises the functions of 1) inducing p53 phosphorylation at the Ser46 residue, a process thought to be the upstream signal for the induction of p53-dependent apoptosis caused by DNA damage such as double-strand breaks, or 2) inducing the expression of a "p53AIP1" protein in the induction of apoptosis. Thus it is possible that compounds selected by the screening methods of this invention can be used to regulate the action of p53 in switching to the apoptosis action amongst the variety of p53 actions, and to control p53-dependent apoptosis induction, a process mediated by the proteins of this invention. As used herein, "regulate" also includes "enhance", "inhibit" or "suppress". Therefore, an apoptosis-enhancing compound may be applied as an agent capable of actively inducing apoptosis of neoplasms such as tumors, and an apoptosis-inhibiting or suppressing compound may be applied as a preventative or therapeutic agent for disorders in p53DINP1-mediated apoptosis.

The present invention also relates to another method of screening candidate compounds for a second apoptosis-regulating agent. This screening method of this invention comprises the steps of: (a) contacting a test sample with a cell containing a vector having the structure in which the p53-binding sequence in the p53DINP1 genome sequence and a reporter gene are operably linked; (b) measuring the expression level of said reporter gene, and (c) selecting a compound capable of decreasing or increasing the expression level of said reporter gene measured in step (b), compared to that measured in the absence of the test sample.

The expression "p53-binding sequence" used herein refers to a sequence in the p53DINP1 genomic DNA to which p53 protein binds to induce transcription of a "p53DINP1" gene, a p53 protein target gene. A specific example of this sequence is shown in SEQ ID NO: 8.

There is no particular limitation as to the type of reporter gene to be used in this invention as long as its expression is detectable. Any reporter gene typically used in various assay systems by those skilled in the art can be employed, for example, the luciferase gene, the chloramphenicol acetyl transferase (CAT) gene, or the β-galactosidase gene.

Herein, "operably linked" means that the binding sequence and the reporter gene are linked such that binding of p53 to the p53-binding sequence triggers induction of reporter gene expression. Preferably, a minimal promoter sequence is arranged upstream of the reporter gene, and the p53-binding sequence is further upstream of this promoter sequence.

There is no particular limitation as to the type of cells which can be used for a screening of the present invention, and for example, cell lines available from American Type Culture Collection (ATCC) such as the SW480 colorectal adenocarcinoma cell line, H1299 non small lung carcinoma cell line, and MCF7 mammary carcinoma cell line can be used. A variety of methods known to those skilled in the art, for example, the use of electroporation and lipofectin reagent, can be used for the transduction of cells with a vector. The above-described reporter gene expression level can be measured by methods generally used by those skilled in the art and depending on the type of reporter gene used.

A compound that reduces or enhances reporter gene expression level when compared to that measured with the same method in the absence of the test sample, is selected as a candidate compound for an apoptosis-regulating agent. p53 is known to bind to a "p53-binding sequence", activate target gene transcription, and then induce apoptosis. Therefore, candidate compounds that reduce reporter gene expression level in the screening methods of the present invention are expected to be used as apoptosis inhibitors. Candidate compounds that enhance reporter gene expression level may be used as apoptosis accelerators.

Test samples to be screened include extracts of the above-mentioned cells, gene library expression products, synthetic low molecular weight compounds, synthetic peptides, and natural compounds.

When used medicinally, a protein or antibody of the present invention, or a compound isolated by a screening method of this invention, may be directly administered to patients, or administered in a dosage form prepared by drug-manufacturing methods well-known in the art. For example, the dosage form may be prepared by appropriately combining with a pharmaceutically acceptable carrier or medium such as sterilized water, physiological saline, a plant oil, an emulsifier, a suspending agent, a surfactant, or a stabilizer. Administration to patients may be carried out by methods known to those skilled in the art, for example, by intra-arterial, intravenous, or subcutaneous administration, or by intranasal, transbronchial, intramuscular, or oral administration. Although the dosage may vary depending on the route of administration, patient body weight and age, those skilled in the art can appropriately select a suitable dosage. In addition, when the compound is encoded by DNA, gene therapy can be performed using a gene therapy vector into which that DNA has been introduced. Those skilled in the art can select an appropriate dosage and method of administration depending on the patient body weight, age, symptoms, and such.

BRIEF DESCRIPTION OF THE DRAWINGS

FIG. 2 shows (A) a comparison of predicted amino acid sequences encoded by the two cDNAs derived from alternative splicing of p53DINP1 chromosomal DNA (SEQ ID NOs: 2 and 4), and (B) the composition of the cDNAs compared with the genomic DNA.

FIG. 9 represents graphs and photographs showing (A) p53AIP1 expression and p53 Ser46 residue phosphorylation, (B) cell cycle phase distribution, and (C) cells stained in TUNEL analysis, where each was measured after overexpression of both p53 and p53DINP1.

BEST MODE FOR CARRYING OUT THE INVENTION

Example 1

Identification of a Novel Transcript Induced by p53

The differential display method (Takei et al., 1998; Okamura et al., 1999, supra) was applied to identify a novel p53-induced transcript.

The LacSwitch vector system (Stratagene) (Wyborski and Short, 1991) was used as an expression system for p53, and the wild-type p53 gene was inserted into the vector thereof to construct a recombinant expression vector. In the same way, recombinant expression vectors containing a mutant type p53 gene or the chloramphenicol acetyltransferase (CAT) gene were constructed as controls. Each vector thus constructed was used for the transfection of SW480 cells deficient in wild-type p53. Each transfectant was exposed to 5 mM IPTG to induce gene expression, and mRNA was then extracted at zero, eight, 16, 24, 32, and 40 hours after this induction. mRNAs thus extracted and a variety of primer pairs were combined and used for differential display.

Of the several hundred bands detected by this method, a 250 bp DNA fragment was detected in the presence of wild-type p53 with a very strong signal, compared to the controls (data not shown). This fragment is hereinafter designated as 8T250.

This fragment was subcloned and its nucleotide sequence was determined using standard procedures. Comparison with known DNA nucleotide sequences in public databases did not reveal any DNA identical to the novel transcript designated as 8T250.

Figure 1:
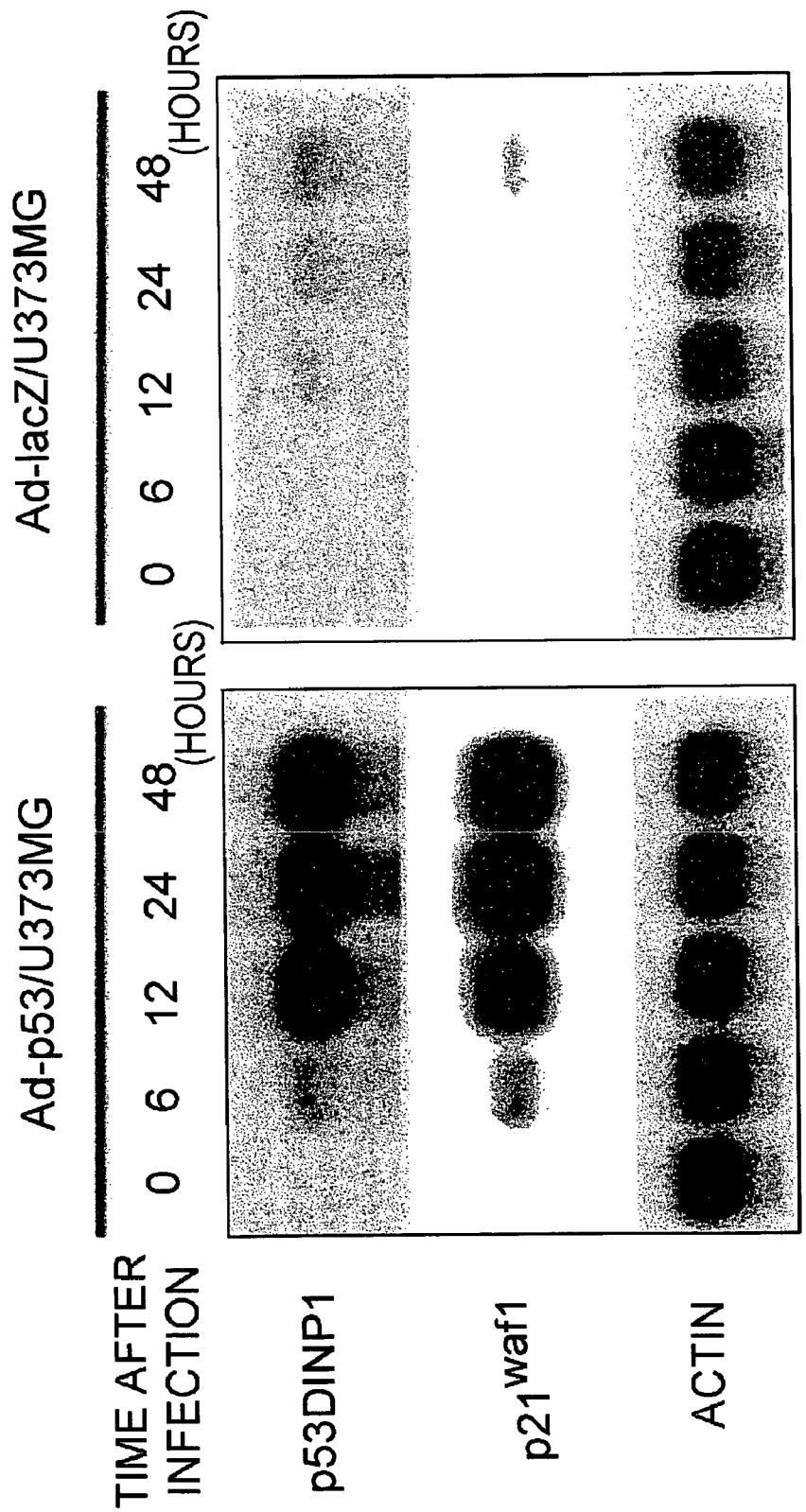
FIG. 1 is a photograph showing the result of Northern blot analysis in Example 1 of p53-induced transcripts along with a positive control (p21$^{waf1}$) and an internal control (actin protein).

In order to confirm the result obtained by the above differential display, RT-PCR and Northern blot analysis were employed using the mRNAs obtained from the above-described SW480 cells, and those obtained from U373MG cells transformed with an adenovirus vector containing the wild-type p53 gene (Ad-p53) or LacZ gene (Ad-LacZ). Northern blot analysis was performed using a known method (el-Deiry, W. S., Nelkin, B. D., Celano, P., Yen, R. W., Falco, J. P., Hamilton, S. R., and Baylin, S. B. (1991). High expression of the DNA methyltransferase gene characterizes human neoplastic cells and progression stages of colon cancer. Proc. Natl. Acad. Sci. U.S.A. 88, 3470-3474). The primers used for RT-PCR were F1 (5'-TTGTGGGT-GAAGTCAGTTCTT-3'/SEQ ID NO: 6) and R1 (5'-GAGCTTCCACTCTGGGACT-3'/SEQ ID NO: 7). In addition, the RT-PCR product obtained using the above primers was used as a probe for Northern blot analysis. FIG. 1 shows the result of Northern blot analysis of the mRNAs prepared using the U373MG cell line.

As shown in FIG. 1, "p53DINP1" transcript expression was specific to cells transfected with Ad-p53, and expression was observed immediately after Ad-p53 transfection. This result thus shows that p53DINP1 gene expression is p53-dependent, and that the transcript is induced immediately after induction by p53. In addition, the expression profile of the p53DINP1 transcript was the same as that of known molecule p21$^{WAF1}$, whose expression is induced by p53.

Using Northern blot analysis, various tissues were then examined for the expression of the above transcript. The sixteen human tissues examined all expressed p53DINP1, and a relatively high level of expression was seen in the pancreas, spleen, testis, and peripheral leukocyte (data not shown). The size of the transcript was estimated to be about 6 kb throughout these experiments.

Example 2

Isolation of the p53DINP1 Gene

In order to isolate a full length cDNA of the novel transcript detected in Example 1, a human thymus-derived cDNA library ($1\times10^6$ colonies) was used to screen for the full length cDNA, using the 8T250 DNA fragment as a probe. The sixteen positive colonies obtained in this screening were subjected to nucleotide sequence determination, resulting in the detection of two open reading frames (ORFs). One ORF coded a polypeptide comprising 240 amino acids (SEQ ID NO: 2), and the other coded a polypeptide comprising 164 amino acids (SEQ ID NO: 4). Hereinafter, the gene generating the two ORFs is designated as p53DINP1 (p53-dependent Damage-Inducible Nuclear Protein 1). Hereinafter, the former and latter ORF are designated as genes p53DINP1a and p53DINP1b respectively.

In order to identify the p53DINP1 gene's chromosomal nucleotide sequence, a cosmid clone containing the complete p53DINP1 gene was isolated, and the nucleotide sequence was determined (SEQ ID NO: 5, accession NO: DDBJ/EMBL/GenBank AB062056) FIG. 2(B) shows a comparison of the genomic DNA and the cDNA. The p53DINP1 gene comprises four exons. The two different transcripts (p53DINP1a and p53DINP1b) are generated by alternative splicing. FIG. 2(A) shows a comparison of the amino acid sequences of p53DINP1a (SEQ ID NO: 1 and 2, accession NO: DDBJ/EMBL/GenBank AB017926) and p53DINP1b (SEQ ID NO: 3 and 4, accession NO: DDBJ/EMBL/GenBank AB017927).

More over, FISH analysis revealed that the genomic sequence spans a 15 kb genomic region within the chromosome 8q22 band (data not shown).

Example 3 p53-Binding Site of the p53DINP1 Gene

Figure 3:
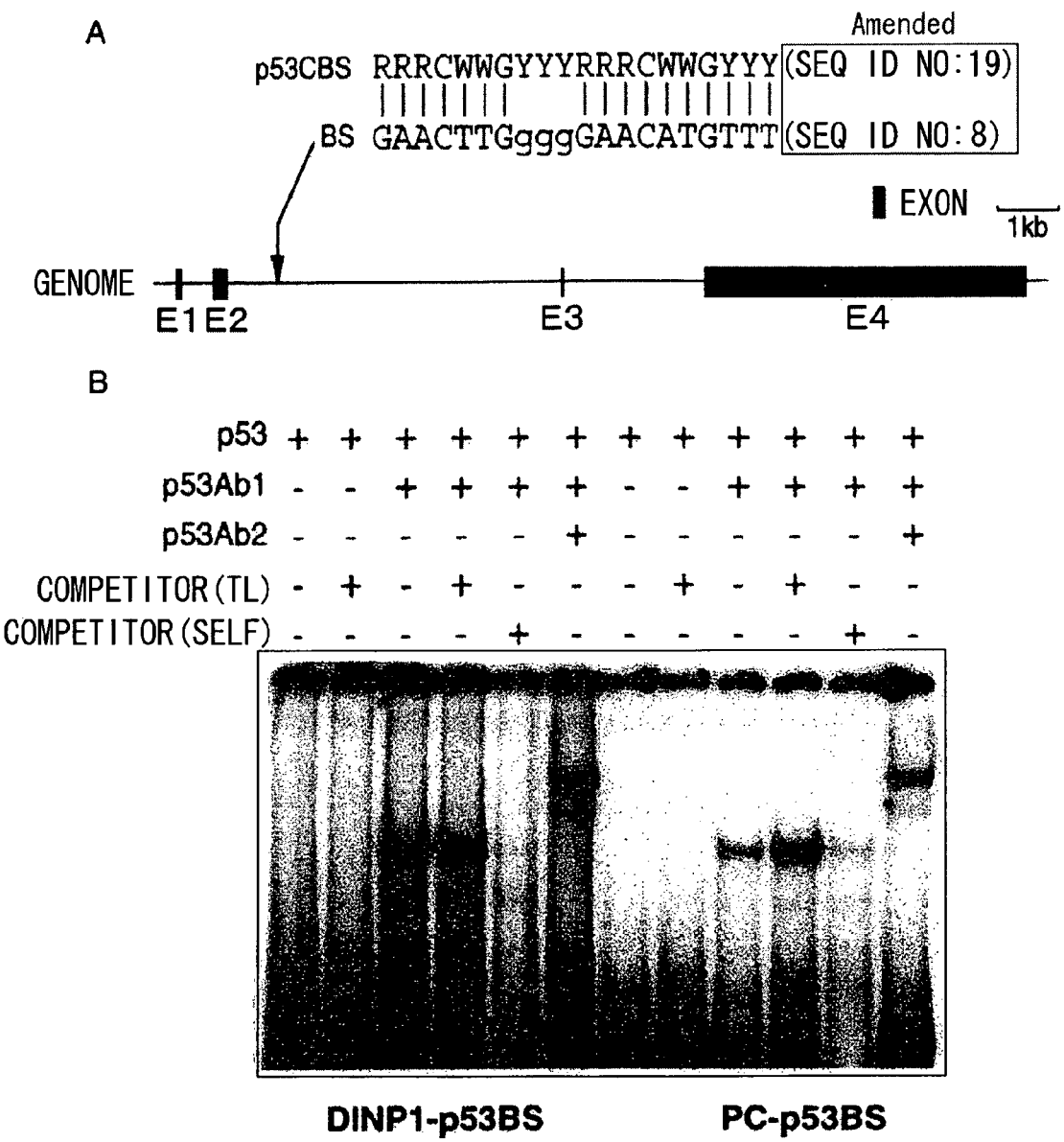
FIG. 3 shows (A) the p53-binding sequence (SEQ ID NOS: 19 and 8, respectively) and its schematic representation, and (B) a photograph of electrophoresis showing the results of EMSA conducted in Example 3.

The inventors found an essential p53-binding site (p53BS) comprising 20 nucleotides (SEQ ID NO: 8) in intron 2 of the p53DINP1 gene. This binding site was 85% identical to the consensus p53-binding sequence (FIG. 3). In order to examine whether p53 binds to oligonucleotides corresponding to the p53BS sequence, electrophoretic-mobility shift assays (EMSA) were employed as described below.

H1299 lung carcinoma cells were infected with a recombinant adenovirus vector that expresses wild-type p53 (Ad-p53), and a nucleic acid extract was then prepared from these infected cells. To this nucleic acid extract was added sonicated salmon sperm DNA (0.5 µg), EMSA buffer, and an appropriate $^{32}$P-labeled double-stranded oligomer (pre-annealed). This mixture was then incubated at room temperature for 30 minutes. The mixture was incubated in the presence of anti-p53 monoclonal antibodies, Pab421 (Oncogene Science) and/or Pab1801 (Santa Cruz Biotechnology). An unlabeled oligonucleotide corresponding to the p53BS sequence (designated as "self" in FIG. 3) or an unlabeled non-specific oligonucleotide (designated as "TL" in FIG. 3) was also added to some samples as a competitor. After incubation, each sample was subjected to electrophoresis on a 4% polyacrylamide gel containing 0.5×TBE. Following electrophoresis the gel was dried and subjected to autoradiography at −80° C. for three hours.

FIG. 3 shows the result of EMSA. Mobility of the 20 bp oligonucleotide shifted when it was mixed with the nucleic acid extract (FIG. 3). An additional mobility shift was observed when anti-p53 monoclonal antibodies p53Ab1 (Pab421) and p53Ab2 (Pab1801) were added to the mixture, indicating that the p53DINP1 gene's 20 bp oligonucleotide sequence is the p53-binding site.

Example 4 p53DINP1 as a Target Gene for p53

To examine whether the p53-binding sequence identified in Example 3 has p53-dependent transcription-enhancing activity, a reporter assay using the luciferase gene was employed as described below.

A 477 bp fragment containing the wild-type p53-binding sequence (GAACTTGGGGGAACATGTTT: SEQ ID NO: 8) within intron 2 was amplified by PCR using primer F (CGCCGAGCTCCCTGCAATACTCACACTGC: SEQ ID NO: 9) and primer R (CAGTACGCGTCCTCCATAAGAC-CCCAATA: SEQ ID NO: 10). The amplified PCR products were then cloned upstream of the SV40 minimal promoter sequence within the pGL3-promoter vector (Promega, Madison, Wis., USA). Hereinafter, the recombinant reporter vector thus obtained is designated as "intron 2-wt".

An oligomer pair corresponding to one copy of the p53-binding sequence, 1F (CGAACTTGGGGGAACAT-GTTTA: SEQ ID NO: 11) and 1R (CGCGTAAACATGT-TCCCCCAAGTTCGAGCT: SEQ ID NO: 12); and another oligomer pair corresponding to two copies of the p53-binding sequence, 2F (CGAACTTGGGGGAACAT-GTTTGAACTTGGGGGAACATGTTTA: SEQ ID NO: 13) and 2R (CGCGTAAACATGTTCCCCCAAGTTCAAA-CATGTTCCCCCAAGTTCGAGCT: SEQ ID NO: 14); were separately and respectively annealed. The annealed oligomer pairs were then ligated with pGL3-promoter vectors that had been cleaved with MluI and XhoI, yielding recombinant reporter vectors (designated as "X1" and "X2" respectively).

A vector comprising a mutation within p53BS ("intron 2-mt") was constructed by using a QuickChange™ Site-Directed Mutagenesis Kit (Stratagene) to introduce a point mutation where p53BS's fourth "C" nucleotide was substituted with "T". The mutant form of the intron 2 fragment (477bp) was cloned into the pGL3-promoter vector in the same way as for the above-mentioned wild-type.

Each recombinant reporter vector thus constructed was used for cotransfection of H1299 lung carcinoma cells (p53 −/−) with a plasmid expressing wild-type or mutant type p53. After transfection with a vector or the like, quantitative and relative final luciferase activities in the cells were measured using a luminometer and according to the attached protocol (Promega).

Figure 4:
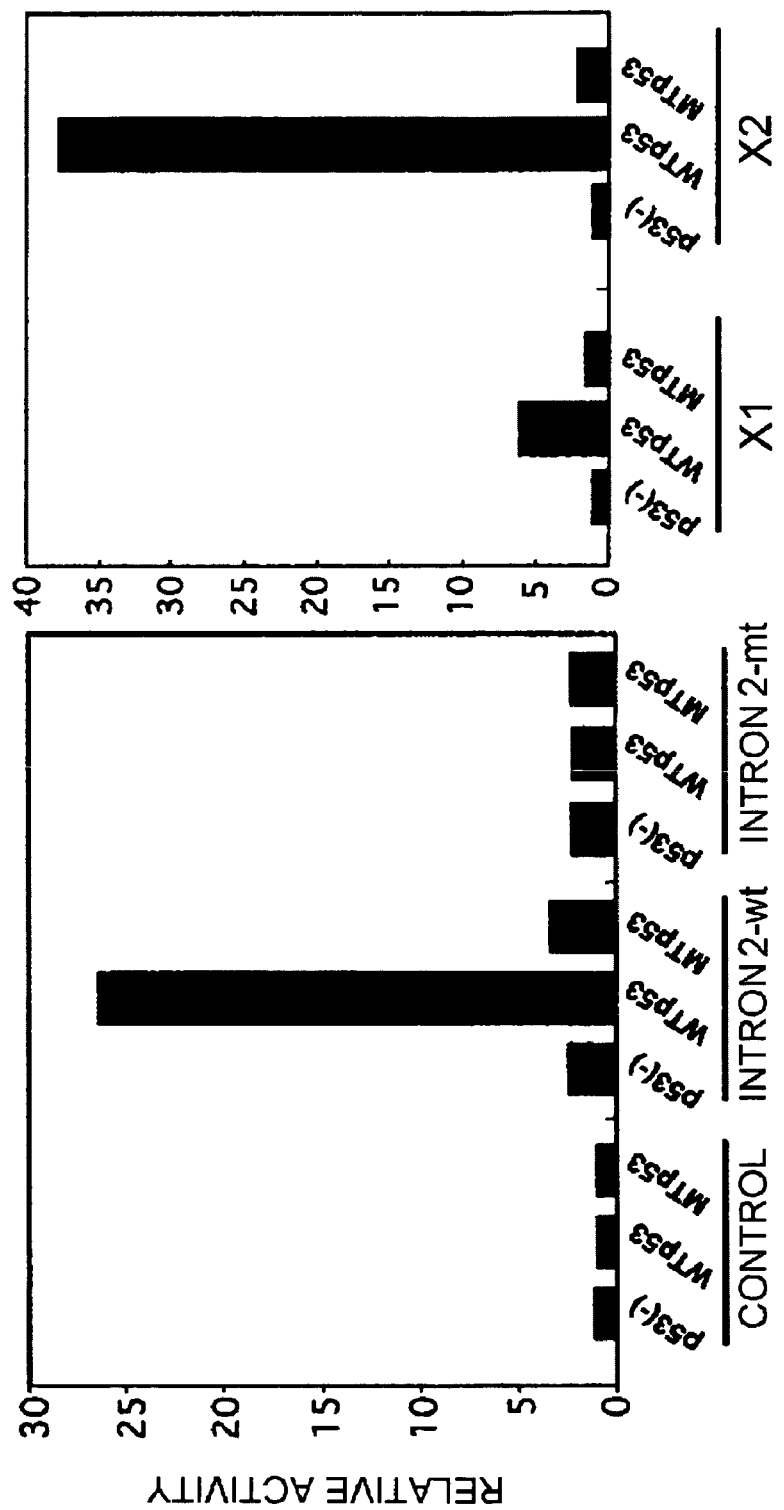
FIG. 4 is a graph showing the transcription inducing activity of the p53-binding sequence from the p53DINP1 gene using the luciferase gene as a reporter gene, as in Example 4.

FIG. 4 shows the results of these measurements. Relative luciferase activity increased significantly when cells were cotransfected with the intron 2-wt reporter vector and the wild-type p53 expression vector. However, this kind of increased activity was not observed when the mutant type p53 or intron 2-mt was introduced.

Luciferase activity increased several times when the X1 reporter vector was introduced with the wild-type p53 expression vector. When the X2 reporter vector was used with wild type p53, luciferase activity increased more than 30 times.

The results from these luciferase assays and from EMSA in Example 3 clearly indicate that p53DINP1 is a direct p53 target.

Example 5

Genotoxic Stress- and p53-Dependent Induction of p53DINP1

Figure 5:
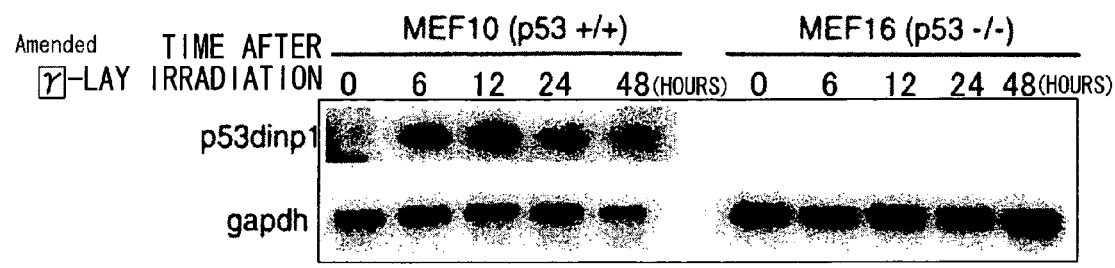
FIG. 5 is a photograph showing confirmation of p53-dependent induction of p53DINP1.

In order to examine whether endogenous p53 induces p53DINP1, mouse p53+/+MEF cells orp53−/−MEF cells were irradiated with γ-rays and expression of the mouse p53DINP1 gene in response to DNA damage was analyzed. FIG. 5 shows these results.

As shown in FIG. 5, there was no sign of p53DINP1 mRNA expression in p53−/−MEF cells following DNA damage. On the other hand, there was a significant increase of p53DINP1 mRNA expression in p53+/+MEF cells in response to DNA damage by γ-ray. These results indicate that DNA damage-induced p53DINP1 expression is dependent on endogenous p53.

An anti-p53DINP1 polyclonal antibody was prepared for use in Western blotting to examine the expression of endogenous p53DINP1 in a human cell line in which a variety of DNA damage had been inflicted.

The above-mentioned anti-p53DINP1 polyclonal antibody was prepared by producing p53DINP1 protein in a recombinant bacterium, using this protein to immunize rabbits using standard methods, harvesting serum from the immunized rabbits, and then affinity-purifying the serum using the above-mentioned p53DINP1 protein.

DNA-damage of the human cell line was carried out as follows: MCF7 cells (mammary carcinoma) and H1299 cells were either treated with 3 µM adriamycin for two hours, or with γ-rays (14 Gy) or UV radiation (10 J/m$^2$). Following this process, each cell-line was cultured in the absence of the damaging agent, and harvested at appropriate intervals. Western blotting was used to measure the expression of p53DINP1 in the damaged cells thus harvested.

For Western blotting, harvested cells were dissolved in a lysis buffer, and a portion (50 µl) of the cell lysate containing soluble cellular proteins was subjected to SDS-polyacrylamide gel electrophoresis. After electrophoresis, the proteins were transferred to a nitrocellulose membrane (HybondT-MECL™). The membrane carrying the separated proteins was treated with a blocking solution containing 5% defatted milk powder (Carnation, Nestle) in TBS-T buffer at room temperature for two hours, and then incubated with anti-p53DINP1 antibody or anti-p53 antibody at room temperature for one hour. After washing, the membrane was incubated with a secondary antibody (peroxidase-bound sheep anti-rabbit Ig antibody), and finally the desired proteins including p53DINP1 were detected using ECL (Amersham Pharmacia Biotech).

Figure 6:
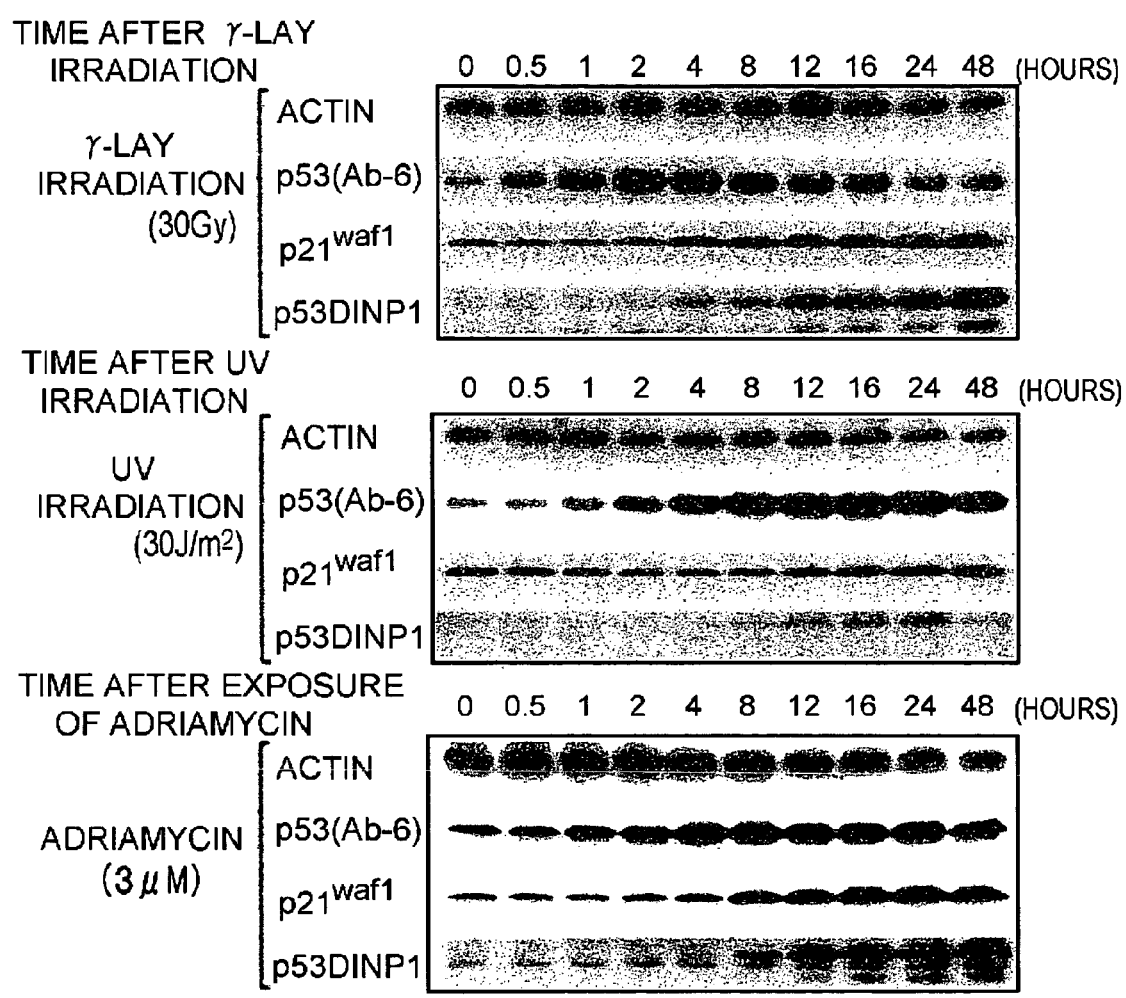
FIG. 6 is a photograph showing confirmation of p53DINP1 induction by double-strand breaks caused by γ-ray irradiation or adriamycin treatment.

As shown in FIG. 6, p53DINP1 expression was significantly induced within four hours of DNA damage by factors triggering double-strand breaks (γ-ray irradiation and adriamycin). p53DINP1 expression was also induced after DNA damage by UV irradiation, however in comparison with other inducers, expression was delayed and relatively moderate.

p53 expression was measured at the same time using the anti-p53 antibody, and was rapid and significant in response to all treatments, regardless of the type of DNA-damaging agent. The difference between expression induction of p53 and p53DINP1 in response to DNA-damaging treatment suggests that induction of the p53DINP1 protein mediates at least two different p53 activation mechanisms.

Example 6 p53DINP1 as a Nuclear Protein

Immunocytometry was carried out to analyze the intracellular localization of p53DINP1 protein in MCF7 cells.

Figure 7:
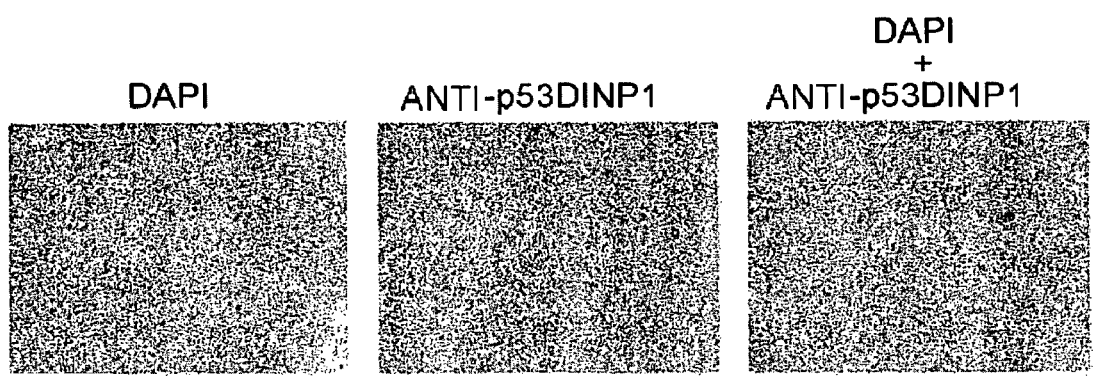
FIG. 7 represents photographs showing the nuclear localization of p53DINP1 protein expression.

MCF7 cells were placed on a poly-D-lysine-coated multi-well chamber slide (Becton Dickinson), and fixed with 4% paraformaldehyde in PBS. The cells were rendered permeable by treatment with 0.2% NP-400 in PBS at room temperature for eight minutes, then blocked in a blocking solution (2.5% horse serum albumin in PBS) at room temperature for 30 minutes. The cells were then incubated with TBS-T containing 1 µg/ml anti-p53DINP1 antibody. This antibody was stained with Congo red-conjugated goat anti-rabbit secondary antibody, followed by DAPI staining. After staining, the cells were viewed with an ECLIPSE E600 microscope (Nikon). As depicted in FIG. 7, cell nuclei staining revealed a clear focus pattern, indicating that p53DINP1 expression is localized to nuclei.

Example 7

Involvement of p53DINP1 in Apoptosis Induced by Double-strand Breaks

In order to clarify the role of p53DINP1 in cell death after DNA damage by double-strand breaks, antisense oligonucleotides (AS1 and AS2) were used in cell damage experiments as follows.

Antisense oligonucleotides AS1 (TGGAACATTGT-TAAGG: SEQ ID NO: 15) and AS2 (TCAGCCTCTGGAA-CAT: SEQ ID NO: 16) were prepared in accordance with the p53DINP1 gene nucleotide sequence and in order to inhibit endogenous p53DINP1 expression. Sense oligonucleotides SE1 (CCTTAACAATGTTCCA: SEQ ID NO: 17) and SE2 (ATGTGCCAGAGGCTGA: SEQ ID NO: 18) were also prepared as controls.

MCF7 cells (2×10$^6$) were plated onto a 10 cmφ dish and the next day the above-prepared antisense or sense oligonucleotides (1 µM) were introduced into cells using Lipofectin reagent (GibcoBRL). The cells were incubated at 37° C. for four hours, the culture medium was replaced, and the cells were then damaged using either γ-irradiation (30 Gy)

or exposure to 3 μM adriamycin. After this genotoxic stress, damaged cells were harvested at appropriate intervals and RNA expression and intracellular proteins were analyzed using RT-PCR and Western blotting respectively.

Figure 8:
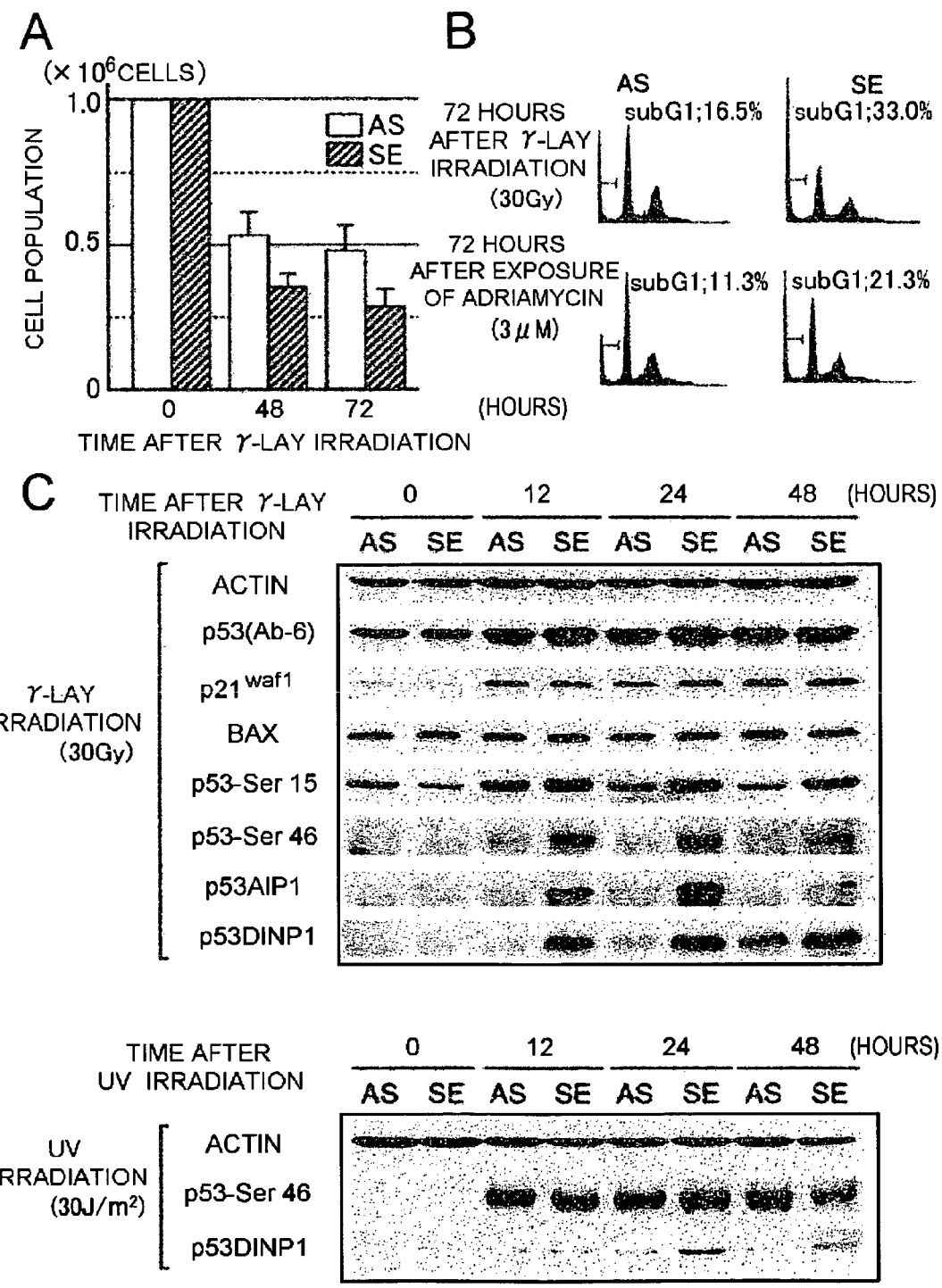
FIG. 8 represents graphs and photographs showing (A) viable cell number, (B) distribution of cell cycle phase, and (C) expression of p53DINP1 and related proteins in cells, where each was measured after DNA damage such as double-strand breaks was inflicted in the presence of the p53DINP1 DNA antisense oligonucleotide (AS) or sense oligonucleotide (SE).

FIG. 8(C) shows the result of Western blotting. From twelve hours after DNA damage (double strand breaks (DSB) caused by γ-irradiation or DNA damage caused by UV-irradiation), the sense oligonucleotide did not affect p53DINP1 protein expression in MCF7 cells. On the other hand, the antisense oligonucleotide (AS2) clearly suppressed this expression.

AS2 and SE2 were then used to examine whether this suppression of p53DINP expression by the antisense oligonucleotide would affect cell death after double-strand breaks. This is outlined below:

AS2 or SE2 were introduced into exponentially growing MCF7 cells and incubated for four hours. These cells were then irradiated with γ-rays (30 Gy) and harvested immediately using trypsin treatment. The damaged cells were diluted to $1 \times 10^6$ cells per dish and maintained in a 6 cmφ dish with fresh medium. The cells were harvested 48 and 72 hours after DNA damage, and cell viability was assessed by staining with 0.4% tripan blue.

As shown in FIG. 8(A), the viability of cells treated with SE2 decreased to 40% or less 48 hours after DNA damage, however increased to 50% or more for cells treated with AS2. Thus, p53DINP1 antisense oligonucleotides can suppress cell death caused by DNA damage, suggesting that p53DINP1 plays a role in apoptosis induction.

Cell viability was then measured using cell cycle analysis. MCF7 cells were damaged as described above, trypsinized 72 hours later, and then washed and fixed with 70% ethanol. The fixed samples were centrifuged, treated with 1 mg/ml RNase and resuspended in 50 μg/ml propidium iodide. The stained cells were then analysed on a FACScan flow cytometer (Beckton-Dickinson).

As FIG. 8(B) shows, 33% of cells treated with SE were dead 72 hours after γ-irradiation (sub-G1), however this was suppressed to 16.5% of cells treated with AS. Similarly, 72 hours after adriamycin treatment, cell death in cells treated with SE was 21.3% or more, but only 11.3% in cells treated with AS. AS pretreatment had no effect on induction of apoptotic cell death caused by UV irradiation (data not shown). These results suggest that p53DINP1 is involved in a p53-dependent apoptosis signal caused by double-strand breaks.

Thus if p53DINP1 is involved in p53-dependent apoptosis, then inhibition of p53DINP1 expression might affect the functions of p53AIP1. Accordingly, the inventors examined whether p53AIP1 expression is induced in AS- or SE-treated MCF7 cells after DNA damage caused by γ-irradiation or adriamycin treatment.

At the same time, expression levels of other p53 target genes and apoptosis-related genes were measured in MCF7 cells using the same methods as described above. FIG. 8(C) shows the results. Of the genes tested, only p53AIP1 expression was suppressed by inhibition of p53DINP1 expression. There was no sign of change in expression of $p21^{Waf1}$, BAX (FIG. 8(C)), caspase-3, caspase-9, and MDM2 (data not shown for these last three).

Thus, since inhibition of p53DINP1 expression by antisense oligonucleotide treatment suppresses cell death in response to double-strand breaks, and also suppresses p53AIP1 expression, it was suggested that p53DINP1 regulates p53AIP1 expression through p53 phosphorylation at the Ser46 residue. Accordingly, the inventors examined whether the inhibition of p53DINP1 expression by treatment with antisense oligonucleotides affected the phosphorylation of p53 protein.

MCF7 cells pretreated with AS or SE were damaged with γ-irradiation, harvested at the above-described times, and then subjected to Western blotting analysis using a phosphorylated residue-specific antibody against Ser15, Ser20, or Ser46.

As shown in FIG. 8(C), Ser15 and Ser20 phosphorylation levels (data not shown for Ser20) decreased in parallel with the amount of p53 protein, and inhibition of p53DINP1 expression did not affect phosphorylation. However, Ser46 phosphorylation was almost completely suppressed by the inhibition of p53DINP1 expression caused by AS2 treatment. This result suggests that p53DINP1 activates the p53 protein such that apoptosis is induced by regulation of p53 Ser46 phosphorylation. This result also suggests that such a modification of the p53 protein activates transcription of other apoptosis-inducing genes such as p53AIP1.

In contrast to γ-irradiation, UV irradiation of MCF7 cells pretreated with AS or SE as described above did not suppress p53AIP1 expression, but significantly induced p53 phosphorylation at Ser46, as shown in FIG. 8(C). These results suggest that at least two pathways are involved in p53 Ser46 phosphorylation and p53AIP1 induction; one involved in double-strand breaks, and the other concerning DNA damage caused by UV irradiation and such. p53DINP1 may be involved in the former of these.

Example 8

Enhancement of p53 Ser46 Phosphorylation, p53AIP1 Expression, and Apoptotic Cell Death, by Overexpression of p53 and p53DINP1

To examine the ability of p53DINP1 to induce apoptosis as a cofactor for p53 Ser46 phosphorylation, the following experiments were conducted. MCF7 cells ($2 \times 10^6$) harboring wild-type p53 protein were plated on a 10 cmφ dish. The next day, the cells were transfected either with a combination of wild-type p53 expression vector and p53DINP1 expression vector (pcDNA3.1(+)/p53DINP1); or a combination of wild-type p53 expression vector and an empty vector for p53DINP1 (pcDNA3.1(+)), using FuGene™ 6 transfection reagent (Roche) according to the attached protocol. The cells were incubated at 37° C. for four hours. To activate p53, the DNA of the cells was then damaged using γ-irradiation (30 Gy) or exposure to 3 μM adriamycin. Following administration of this genotoxic stress, damaged cells were harvested at a variety of times and analyzed using RT-PCR, Western blotting, cell cycle analysis, and TUNEL assays. TUNEL (terminal transferase-mediated dUTP nick end-labelling) assays were performed in situ using Apoptag Direct (Oncor) according to the attached protocol. Finally, cells were stained with propidium iodide and immunofluorescence was viewed using an ECLIPSE E600 microscope (Nikon).

As FIG. 9(A) illustrates, Western blotting analysis revealed that overexpression of both p53DINP1 and p53 stimulated induction of p53 Ser46 phosphorylation and p53AIP1 expression. FIG. 9(B and C) shows the results of apoptotic cell number evaluation. TUNEL analysis (FIG. 9(C)) and FACS analysis (FIG. 9(B)) revealed that overexpression of both p53DINP1 and p53 significantly increased the proportion of apoptotic cells by 72 hours after the administration of genotoxic stress to induce double-strand breaks.

Example 9

Interaction of p53DINP1 with p53-Ser46 Kinase

In order to clarify the governing mechanism of p53DINP1-mediated Ser46-phosphorylation of p53, in vitro kinase analysis was performed using immunoprecipitated p53DINP1 and GST-p53.

p53DINP1 and its related proteins were immunoprecipitated from the cell lysate of MCF7 cells, which were either treated or untreated with radiation, using a rabbit anti-p53DINP1 polyclonal antibody. The phosphorylation activity of the resultant precipitates was then analyzed. The p53DINP1-specific antibody used in this experiment had previously been used to effectively precipitate p53DINP1 from crude cell lysates (data not shown).

Figure 10:
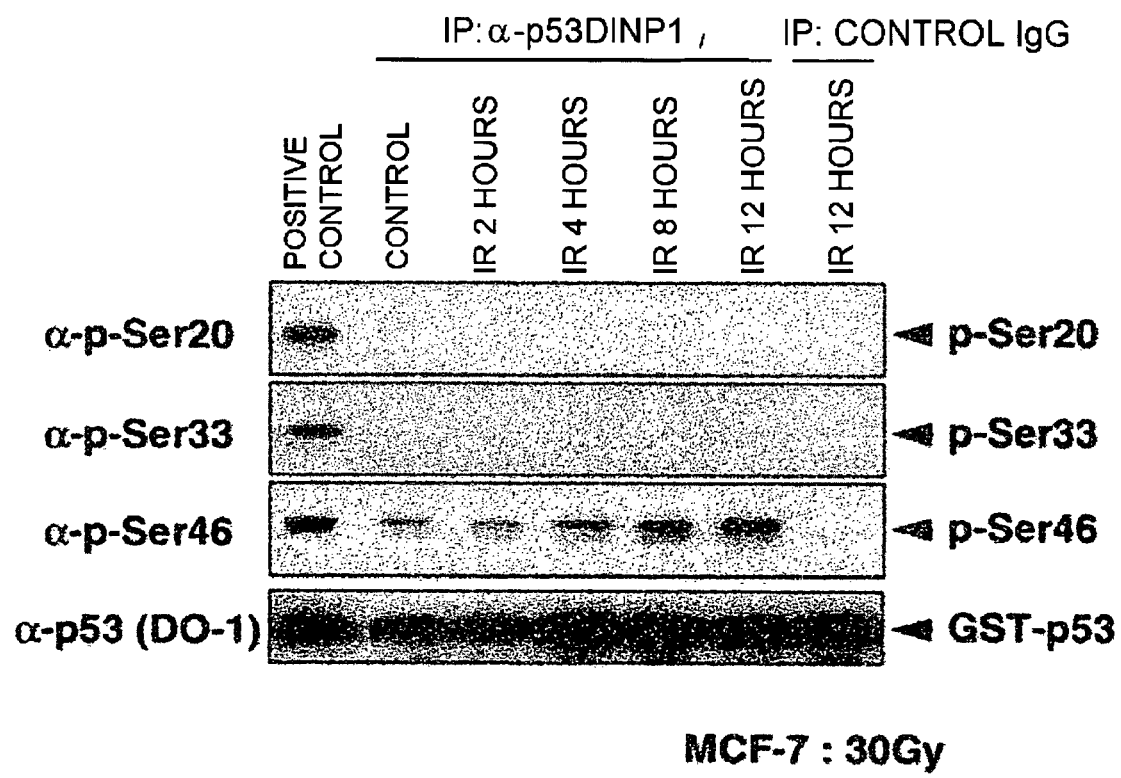
FIG. 10 represents a photograph showing recovery of a p53 Ser46 kinase by immunoprecipitation using the anti-p53DINP1 antibody.

As shown in FIG. 10, Ser46 phosphorylation was clearly accelerated in immunoprecipitates prepared from cell lysates isolated four, eight, and twelve hours after cell damage. In contrast, Ser46 kinase activity was not observed in the control, which comprised using rabbit IgG prepared prior to immunization to immunoprecipitate proteins from cells isolated twelve hours after cell damage ("control IgG" in FIG. 10).

p53DINP1's specificity to Ser46 phosphorylation was evaluated by analyzing p53 phosphorylated at Ser20 and Ser33 using the rabbit polyclonal antibodies p53-P-Ser20 (which recognizes Ser20-phosphorylation of p53) and p53-P-Ser33 (which recognizes Ser33-phosphorylation of p53).

Ser33 is reported to be another possible phosphorylation site which is important in p53-dependent apoptosis (Bulavin, D. V., Saito, S., Hollander, M. C., Sakaguchi, K., Anderson, C. W., Appella, E., and Fornace, A. J. Jr. (1999). Phosphorylation of human p53 by p38 kinase coordinates N-terminal phosphorylation and apoptosis in response to UV irradiation. EMBO J. 18, 6845-6854). However, as FIG. 9 indicates, phosphorylation of Ser20 and Ser33 was not observed in analysis of whole cell lysates derived from irradiated MCF7 cells. The result suggests that p53DINP1 is involved in the specific phosphorylation of Ser46. Results from the immunoprecipitation experiment using the rabbit anti-p53DINP1 antibody also suggest that the kinase which phosphorylates p53 at Ser46 also interacts with p53DINP1 in response to DNA damage.

INDUSTRIAL APPLICABILITY

The present invention provides "p53DINP1", a novel target gene for the p53 tumor suppressor protein. This gene is closely associated with p53-mediated apoptosis caused by DNA damage such as double-strand breaks. This gene is particularly involved in phosphorylation of p53 at Ser46, an upstream signal in the apoptosis pathway. Therefore, the p53DINP1 gene and p53DINP1 protein of the present invention would be useful as a tool for research into the induction of p53-dependent apoptosis, and also for apoptosis-mediated therapy for human cancer cells by introducing the gene of the present invention into cancer cells using an expression vector or an adenovirus vector. The p53DINP1 gene of the present invention, and the protein encoded by this gene, can also be used as target molecules in the development of therapeutic agents for apoptosis-associated diseases.

The present invention also provides a method of screening for candidate compounds that can control apoptosis induction. Thus, the development of preventive and therapeutic agents that comprise such a compound as their effective component, for both cancers and apoptosis-associated diseases, are greatly expected.

---

The invention claimed is:

1. An isolated DNA of the following (a) or (b):
   (a) a DNA encoding a protein comprising the amino acid sequence of SEQ ID NO: 2, or
   (b) a DNA consisting of the coding region of the nucleotide sequence of SEQ ID NO: 1.

2. A vector comprising the DNA of claim 1.

3. An isolated host cell comprising the DNA of claim 1, or the vector of claim 2.

4. An isolated host cell comprising the vector of claim 2.

* * * * *

SEQUENCE LISTING

```
<160> NUMBER OF SEQ ID NOS: 18

<210> SEQ ID NO 1
<211> LENGTH: 5313
<212> TYPE: DNA
<213> ORGANISM: Homo sapiens
<220> FEATURE:
<221> NAME/KEY: CDS
<222> LOCATION: (40)..(762)
<223> OTHER INFORMATION: /codon_start=1
      /gene="p53DINP1"
      /product="p53DINP1a"
<220> FEATURE:
<221> NAME/KEY: misc_feature
<222> LOCATION: (1691)
<223> OTHER INFORMATION: n= A, T, C, or G

<400> SEQUENCE: 1
taaaagacat ccagccaaac tctcagtctt gccttaaca atg ttc cag agg ctg         54
                                           Met Phe Gln Arg Leu
                                            1               5 aat aaa atg ttt gtg ggt gaa gtc agt tct tcc tcc aac caa gaa cca       102
Asn Lys Met Phe Val Gly Glu Val Ser Ser Ser Ser Asn Gln Glu Pro
             10                  15                  20 gaa ttc aat gag aaa gaa gat gat gaa tgg att ctt gtt gac ttc ata       150
Glu Phe Asn Glu Lys Glu Asp Asp Glu Trp Ile Leu Val Asp Phe Ile
         25                  30                  35 gat act tgc act ggt ttc tca gca gaa gaa gaa gaa gaa gag gag gac       198
```

```
                                                                -continued

Asp Thr Cys Thr Gly Phe Ser Ala Glu Glu Glu Glu Glu Asp
     40                  45                  50 atc agt gaa gag tca cct act gag cac cct tca gtc ttt tcc tgt tta    246
Ile Ser Glu Glu Ser Pro Thr Glu His Pro Ser Val Phe Ser Cys Leu
     55                  60                  65 ccg gca tct ctt gag tgc ttg gct gat aca agt gat tcc tgc ttt ctc    294
Pro Ala Ser Leu Glu Cys Leu Ala Asp Thr Ser Asp Ser Cys Phe Leu
 70                  75                  80                  85 cag ttt gag tca tgt cca atg gag gag agc tgg ttt atc acc cca ccc    342
Gln Phe Glu Ser Cys Pro Met Glu Glu Ser Trp Phe Ile Thr Pro Pro
                 90                  95                 100 cca tgt ttt act gca ggt gga tta acc act atc aag gtg gaa aca agt    390
Pro Cys Phe Thr Ala Gly Gly Leu Thr Thr Ile Lys Val Glu Thr Ser
            105                 110                 115 cct atg gaa aac ctt ctc att gaa cat ccc agc atg tct gtc tat gct    438
Pro Met Glu Asn Leu Leu Ile Glu His Pro Ser Met Ser Val Tyr Ala
        120                 125                 130 gtg cat aac tcc tgc cct ggt ctc agt gag gcc acc cgt ggg act gat    486
Val His Asn Ser Cys Pro Gly Leu Ser Glu Ala Thr Arg Gly Thr Asp
    135                 140                 145 gaa tta cat agc cca agt agt ccc aga gtg gaa gct caa aat gaa atg    534
Glu Leu His Ser Pro Ser Ser Pro Arg Val Glu Ala Gln Asn Glu Met
150                 155                 160                 165 ggg cag cat att cat tgt tat gtt gca gct ctt gct gct cat aca act    582
Gly Gln His Ile His Cys Tyr Val Ala Ala Leu Ala Ala His Thr Thr
                170                 175                 180 ttt ctg gaa caa ccc aag agc ttt cgc cct tcc cag tgg ata aaa gaa    630
Phe Leu Glu Gln Pro Lys Ser Phe Arg Pro Ser Gln Trp Ile Lys Glu
            185                 190                 195 cac agt gaa aga cag cct ctt aac aga aat agc ctt cgt cgc caa aat    678
His Ser Glu Arg Gln Pro Leu Asn Arg Asn Ser Leu Arg Arg Gln Asn
        200                 205                 210 ctt acc agg gat tgc cac cct cgg caa gtc aag cac aat ggc tgg gtt    726
Leu Thr Arg Asp Cys His Pro Arg Gln Val Lys His Asn Gly Trp Val
    215                 220                 225 gtt cat cag ccc tgc ccg cgt cag tac aat tac taa tagtttcaag          772
Val His Gln Pro Cys Pro Arg Gln Tyr Asn Tyr
230                 235                 240 ttttgttggt tggtttctct tggtttgtgc taacatgtat ggatgtgtgt atatgtacag   832
tgaaaatgtt gtctctttac aaccaattga taaccaatca catagtttta tcagtgtatt   892
tagacactat cttgaaaatc agatttatat gctgtgtatc acataatgcc ttgcctttaa   952
catttacttt ttttgtacac tttttcagat tatttctgga acatatcaa tataattaca    1012 gtgtttgggg gtgtctttaa atatattagg ttatacatta gtcagcattt taaagacatt   1072
tcttcccaag tacgagaata ggcatctttc attttcattt tattttgtat tacttaatct   1132
tttaagcaag caaaaattta ttctcagggt cagctgtaca cttttattgac cagtacttga  1192 taatctctct gtatatgatg aatacatttt tatacactaa cattagcatt aacaggtgat   1252
agttgccatg gatataatgg aattatggct ggactttctt ttgaaagaaa acttgatgta   1312
ttctgtgtgt atggtttttc cccagattag tcatacagtt catttggaat tcaggtacat   1372
taagctttag tgaagagtgc atgcagtaat ccaatgtga ctgcatgacg tggtacagac    1432
attacaggtg ttgtagacag aggcacttgt ctcgtgcaga gggattaaat tagacctgtg   1492
agattatatt tggaaaaatt catgtctgta actaacccat tagtgcagta tttaatttgt   1552
tactattcct tcccgccaat tctgtccact cctcacctcg catcagctat aaatttggaa   1612
```

```
atacttgtcc aggcactcaa gtgacttcat atttctctct gcccatggga aaagagatag   1672
gctttatatt tccacagant gaaaaatcct ctgtcatgga gcctgtcctg ccaagtggca   1732
agaatgtggg gactgtctgg tgatgatgtc tttcatggca tctgagtgaa gaatgacagg   1792
ttggctcaac ttttttcttt ttttttttta attgccttgt attgtaagta ttcttccctg   1852
cagtccaagt gacttttcat tttttgtttt aacttcaggc aaaatcttta accactctgg   1912
cctctgtttc ccccaccaac ggggagcagt gacatttacc tccctcacag agtcactgtg   1972
aggattctat actgatttga agtggagctg ttcagaactg aaccttgtag gaaattccaa   2032
gggcctttct actgaatctg gtgatggggt ggggccgtgg cactttctct gccacagctg   2092
ttcttcacag tgttggtgct aatgaggcca gggtgcaggg ttcgattcac acgtaggcca   2152
gttaacttag agaaaatcta tttccttacc tctagccagt cacttccttt ttccgcagtt   2212
gtgatgggtt ttgctgagcc atccactctg actgatttcc tctgaagtaa acatatttac   2272
aatccaaagc aattctactg acagaagtgt tgccttcata atcaaacagc ttgttttttcc  2332
atctcctctg caaccctaat taaatgagta caggtctaca aaatgttttc aaggagaaaa   2392
gcagcatatc cttaagtgaa gtattatatt tttcaataac cctgtagtgg cttgatgcag   2452
ggaaccctgg gggactttca gcgaagagct gtgctctttt ctgactagat tagagcgttt   2512
ggagtggaag acgtcaaatg tgtagtgaga tggaggtttt acattgttct tctactggct   2572
gtgatgaagt gccagaatgt ctctttagaa caagagttag attccccctt tctccttatt   2632
gccccttccg ttttgacttc ccctttattt atttgctgtc taattagggg ccaagtctgt   2692
aaagttttgt caaagtgagt tagaagttgt ttttcttac tatttgtgtt taccagagtt     2752
gggagataag atagtttcca tgaaggtgtg tatgttttat acgatgtttg ttatagggcc   2812
atgcattggt aacttgaaaa taagacagct taatgtcttc aggatgtaat cagacagctt   2872
aatgtcttca gggatgtaaa actctgacta cacggcgtct cttttcata cattgcatgt     2932
aagttgttag tacctcacaa gctacagaag ttcagccatg agattttgtt tggcaacatg   2992
aacagatttg tgtataactg caatggcctt ttttccagat ttccttattg acttttttgtt  3052
tgccttacct ggggctagtt ttttatgctt tgtacctaga aaacaaaaaa ttacattcgt   3112
tgggcttttt ttcaaggttg ggattaccac accacctgga atatcatact gtggtttctg   3172
cctaaaattg gcacatgtaa gtattgaaga aaatggttat ataattcagt tgaaactctt   3232
ggttattaga tgttaggcat ctcctgtatg taagacacaa ggccaaccac aacacagaac   3292
gatgttgacc tgttaagtat tctctgaaac atggccaaaa tgcatttat gagctttttt     3352
tttttgctat tgtaaatatt agtggtttac aatgcgcttt aaacatattt ctttaaaatg   3412
caagcagtga gaaataagac ctctctgaat tagtagctct aaactgttaa catagaatgt   3472
tacttggaaa aagtctggaa tatgtggtgt acacaagcag tgcttcgtga atgagtttct   3532
tagcttttat agtgcgccat gtttctcaaa gtttgttttt gttgacaaaa catttataa     3592
tatatatctt atgtttattt tttttctcaa ctaattgtgt actgcactgt aaggtgaaaa   3652
ttagccatcc attatttatc ttctgtggca atgcatttat atggttgatt gggtggggaa   3712
ttttttgcag aaagatgcaa agtgatgggt tttcgacttc ctatcgcagg gagcttttaa   3772
gaaatattaa ttttcctatac attttttccaa tccccatgca aactgttcct gtttacatac   3832
cttctctgtt gtatcagtac tttgagtgag aagacagttt atttaaaact tgagcaggct   3892
gttcagcatt ttttctgctt ctgaaatctg tatagtacac tggtttgtaa tcattatgtc   3952
ttcattgaaa tccttgctac ttctcttcct cctcaatgaa atacattata tattatcttt   4012
```

-continued

```
atgtactctt aagaaaaacg agcaaggaag agtatcttca ttattctcat tttctctgag      4072
ttggaaacaa aaacatgaag gactccaact agaagacaga tatttacatt taaatagatt      4132
agtgggaaaa ctttaagagt ttccacatat tagttttcat tttttgagtc aagagactgc      4192
tccttgtact gggagacact agtagtatat gtttgtaatg ttactttaaa attatctttt      4252 tatttttataa ggcccataaa tactggttaa actctgttaa aagtgggcct tctatcttgg     4312
atggtttcac tgccatcagc catgctgata tattagaaat ggcatcccta tctacttact      4372
ttaatgctta aaattataca taaaatgctt tatttagaaa acctacatga tacagtggtg      4432
tcagccttgc catgtatcag tttcacttga aatttgagac caattaaatt tcaactgttt      4492
agggtggaga aagaggtact ggaaaacatg cagatgagga tatctttat gtgcaacagt       4552 atcctttgca tgggaggaga gttactcttg aaaggcaggc agcttaagtg gacaatgttt      4612
tgtatatagt tgagaatttt acgacacttt taaaaattgt gtaattgtta aatgtccagt      4672
tttgctctgt tttgcctgaa gttttagtat ttgttttcta ggtggacctc tgaaaaccaa      4732
accagtacct ggggaggtta gatgtgtgtt tcaggcttgg agtgtatgag tggttttgct      4792
tgtattttcc tccagagatt ttgaacttta ataattgcgt gtgtgttttt tttttttta       4852 agtggctttg ttttttttttc tcaagtaaaa ttgtgaacat atttcccttta taggggcagg    4912 gcatgagtta gggagactga agagtattgt agactgtaca tgtgccttct taatgtgttt     4972
ctcgacacat tttttttcag taacttgaaa attcaaaagg gacatttggt taggttactg     5032
tacatcaatc tatgcataaa tggcagcttg ttttcttgag ccacggtcta aattttgttt    5092
ttatagaaat tttttatact gattggttca tagatggtca gttttgtaca cagactgaac    5152
aatacagcac tttgccaaaa atgagtgtag cattgtttaa acattgtgtg ttaacacctg    5212
ttctttgtaa ttgggttgtg gtgcattttg cactacctgg agttacagtt ttcaatctgt    5272
cagtaaataa agtgtccttt aacttcaaaa aaaaaaaaa a                         5313
```

<210> SEQ ID NO 2
<211> LENGTH: 240
<212> TYPE: PRT
<213> ORGANISM: Homo sapiens

<400> SEQUENCE: 2

```
Met Phe Gln Arg Leu Asn Lys Met Phe Val Gly Glu Val Ser Ser Ser
 1               5                  10                  15

Ser Asn Gln Glu Pro Glu Phe Asn Glu Lys Asp Asp Glu Trp Ile
            20                  25                  30

Leu Val Asp Phe Ile Asp Thr Cys Thr Gly Phe Ser Ala Glu Glu Glu
        35                  40                  45

Glu Glu Glu Glu Asp Ile Ser Glu Glu Ser Pro Thr Glu His Pro Ser
    50                  55                  60

Val Phe Ser Cys Leu Pro Ala Ser Leu Glu Cys Leu Ala Asp Thr Ser
65                  70                  75                  80

Asp Ser Cys Phe Leu Gln Phe Glu Ser Cys Pro Met Glu Glu Ser Trp
                85                  90                  95

Phe Ile Thr Pro Pro Cys Phe Thr Ala Gly Gly Leu Thr Thr Ile
            100                 105                 110

Lys Val Glu Thr Ser Pro Met Glu Asn Leu Leu Ile Glu His Pro Ser
        115                 120                 125

Met Ser Val Tyr Ala Val His Asn Ser Cys Pro Gly Leu Ser Glu Ala
    130                 135                 140
```

-continued

```
Thr Arg Gly Thr Asp Glu Leu His Ser Pro Ser Ser Pro Arg Val Glu
145                 150                 155                 160

Ala Gln Asn Glu Met Gly Gln His Ile His Cys Tyr Val Ala Ala Leu
                165                 170                 175

Ala Ala His Thr Thr Phe Leu Glu Gln Pro Lys Ser Phe Arg Pro Ser
            180                 185                 190

Gln Trp Ile Lys Glu His Ser Glu Arg Gln Pro Leu Asn Arg Asn Ser
        195                 200                 205

Leu Arg Arg Gln Asn Leu Thr Arg Asp Cys His Pro Arg Gln Val Lys
    210                 215                 220

His Asn Gly Trp Val Val His Gln Pro Cys Pro Arg Gln Tyr Asn Tyr
225                 230                 235                 240
```

<210> SEQ ID NO 3
<211> LENGTH: 5351
<212> TYPE: DNA
<213> ORGANISM: Homo sapiens
<220> FEATURE:
<221> NAME/KEY: CDS
<222> LOCATION: (40)..(534)
<223> OTHER INFORMATION: /codon_start=1
      /gene="p53DINP1"
      /product="p53DINP1b"
<220> FEATURE:
<221> NAME/KEY: misc_feature
<222> LOCATION: (535)
<223> OTHER INFORMATION: n=A, T, C, or G
<220> FEATURE:
<221> NAME/KEY: misc_feature
<222> LOCATION: (1729)
<223> OTHER INFORMATION: n= A, T, C, or G

<400> SEQUENCE: 3

```
taaaagacat ccagccaaac tctcagtctt gccttaaca atg ttc cag agg ctg         54
                                            Met Phe Gln Arg Leu
                                              1               5 aat aaa atg ttt gtg ggt gaa gtc agt tct tcc tcc aac caa gaa cca        102
Asn Lys Met Phe Val Gly Glu Val Ser Ser Ser Ser Asn Gln Glu Pro
         10                  15                  20 gaa ttc aat gag aaa gaa gat gat gaa tgg att ctt gtt gac ttc ata        150
Glu Phe Asn Glu Lys Glu Asp Asp Glu Trp Ile Leu Val Asp Phe Ile
             25                  30                  35 gat act tgc act ggt ttc tca gca gaa gaa gaa gaa gaa gag gag gac        198
Asp Thr Cys Thr Gly Phe Ser Ala Glu Glu Glu Glu Glu Glu Glu Asp
         40                  45                  50 atc agt gaa gag tca cct act gag cac cct tca gtc ttt tcc tgt tta        246
Ile Ser Glu Glu Ser Pro Thr Glu His Pro Ser Val Phe Ser Cys Leu
     55                  60                  65 ccg gca tct ctt gag tgc ttg gct gat aca agt gat tcc tgc ttt ctc        294
Pro Ala Ser Leu Glu Cys Leu Ala Asp Thr Ser Asp Ser Cys Phe Leu
 70                  75                  80                  85 cag ttt gag tca tgt cca atg gag gag agc tgg ttt atc acc cca ccc        342
Gln Phe Glu Ser Cys Pro Met Glu Glu Ser Trp Phe Ile Thr Pro Pro
                 90                  95                 100 cca tgt ttt act gca ggt gga tta acc act atc aag gtg gaa aca agt        390
Pro Cys Phe Thr Ala Gly Gly Leu Thr Thr Ile Lys Val Glu Thr Ser
            105                 110                 115 cct atg gaa aac ctt ctc att gaa cat ccc agc atg tct gtc tat gct        438
Pro Met Glu Asn Leu Leu Ile Glu His Pro Ser Met Ser Val Tyr Ala
        120                 125                 130 gtg cat aac tcc tgc cct ggt ctc agt gag gcc acc cgt ggg act gat        486
Val His Asn Ser Cys Pro Gly Leu Ser Glu Ala Thr Arg Gly Thr Asp
```

|   |   |   |
|---|---|---|
| 135 | 140 | 145 |

| gaa tta cat agc cca agt agt ccc agg gcc agg aaa agc tgc tta taa | 534 |
| Glu Leu His Ser Pro Ser Ser Pro Arg Ala Arg Lys Ser Cys Leu | |
| 150 155 160 165 | |
| nactcacggg cacagaagtg gaagctcaaa atgaaatggg gcagcatatt cattgttatg | 594 |
| ttgcagctct tgctgctcat acaacttttc tggaacaacc caagagcttt cgcccttccc | 654 |
| agtggataaa agaacacagt gaaagacagc ctcttaacag aaatagcctt cgtcgccaaa | 714 |
| atcttaccag ggattgccac cctcggcaag tcaagcacaa tggctgggtt gttcatcagc | 774 |
| cctgcccgcg tcagtacaat tactaatagt ttcaagtttt gttggttggt ttctcttggt | 834 |
| ttgtgctaac atgtatggat gtgtgtatat gtacagtgaa atgttgtct ctttacaacc | 894 |
| aattgataac caatcacata gttttatcag tgtatttaga cactatcttg aaaatcagat | 954 |
| ttatatgctg tgtatcacat aatgccttgc ctttaacatt tactttttt gtacactttt | 1014 |
| tcagattatt tctggaaaca tatcaatata attacagtgt ttgggggtgt ctttaaatat | 1074 |
| attaggttat acattagtca gcattttaaa gacatttctt cccaagtacg agaataggca | 1134 |
| tctttcattt tcatttttatt ttgtattact taatctttta agcaagcaaa aatttattct | 1194 |
| cagggtcagc tgtacacttt attgaccagt acttgataat ctctctgtat atgatgaata | 1254 |
| cattttata cactaacatt agcattaaca ggtgatagtt gccatggata taatggaatt | 1314 |
| atggctggac tttcttttga aagaaaactt gatgtattct gtgtgtatgg ttttccca | 1374 |
| gattagtcat acagttcatt tggaattcag gtacattaag ctttagtgaa gagtgcatgc | 1434 |
| agtaattcca atgtgactgc atgacgtggt acagacatta caggtgttgt agacagaggc | 1494 |
| acttgtctcg tgcagaggga ttaaattaga cctgtgagat tatatttgga aaaattcatg | 1554 |
| tctgtaacta acccattagt gcagtattta atttgttact attccttccc gccaattctg | 1614 |
| tccactcctc acctcgcatc agctataaat ttggaaatac ttgtccaggc actcaagtga | 1674 |
| cttcatattt ctctctgccc atgggaaaag agataggctt tatatttcca cagantgaaa | 1734 |
| aatcctctgt catggagcct gtcctgccaa gtggcaagaa tgtggggact gtctggtgat | 1794 |
| gatgtctttc atggcatctg agtgaagaat gacaggttgg ctcaacttt ttctttttt | 1854 |
| ttttaattg ccttgtattg taagtattct tccctgcagt ccaagtgact tttcattttt | 1914 |
| tgttttaact tcaggcaaaa tctttaacca ctctggcctc tgtttccccc accaacgggg | 1974 |
| agcagtgaca tttacctccc tcacagagtc actgtgagga ttctatactg atttgaagtg | 2034 |
| gagctgttca gaactgaacc ttgtaggaaa ttccaagggc cttttctactg aatctggtga | 2094 |
| tggggtgggg ccgtggcact ttctctgcca cagctgttct tcacagtgtt ggtgctaatg | 2154 |
| aggccagggt gcagggttcg attcacacgt aggccagtta acttagagaa aatctatttc | 2214 |
| cttacctcta gccagtcact tccttttcc gcagttgtga tgggttttgc tgagccatcc | 2274 |
| actctgactg atttcctctg aagtaaacat atttacaatc caaagcaatt ctactgacag | 2334 |
| aagtgttgcc ttcataatca aacagcttgt ttttccatct cctctgcaac cctaattaaa | 2394 |
| tgagtacagg tctacaaaat gttttcaagg agaaaagcag catatcctta agtgaagtat | 2454 |
| tatatttttc aataaccctg tagtggcttg atgcagggaa ccctggggga ctttcagcga | 2514 |
| agagctgtgc tcttttctga ctagattaga gcgtttggga tggaagacgt caaatgtgta | 2574 |
| gtgagatgga ggttttacat tgttcttcta ctggctgtga tgaagtgcca gaatgtctct | 2634 |
| ttagaacaag agttagattc ccccttctc cttattgccc cttccgtttt gacttcccct | 2694 |
| ttatttattt gctgtctaat taggggccaa gtctgtaaag ttttgtcaaa gtgagttaga | 2754 |

-continued

```
agttgttttt tcttactatt tgtgtttacc agagttggga gataagatag tttccatgaa    2814
ggtgtgtatg ttttatacga tgtttgttat agggccatgc attggtaact gaaaataag    2874
acagcttaat gtcttcagga tgtaatcaga cagcttaatg tcttcaggga tgtaaaactc    2934
tgactacacg gcgtctcttt ttcatacatt gcatgtaagt tgttagtacc tcacaagcta    2994
cagaagttca gccatgagat tttgtttggc aacatgaaca gatttgtgta taactgcaat    3054
ggccttttt ccagatttcc ttattgactt tttgtttgcc ttacctgggg ctagtttttt    3114
atgctttgta cctagaaaac aaaaaattac attcgttggg cttttttca aggttgggat    3174
taccacacca cctggaatat catactgtgg tttctgccta aaattggcac atgtaagtat    3234
tgaagaaaat ggttatataa ttcagttgaa actcttggtt attagatgtt aggcatctcc    3294
tgtatgtaag acacaaggcc aaccacaaca cagaacgatg ttgacctgtt aagtattctc    3354
tgaaacatgc ccaaaatgca ttttatgagc tttttttttt tgctattgta aatattagtg    3414
gtttacaatg cgctttaaac atatttcttt aaaatgcaag cagtgagaaa taagacctct    3474
ctgaattagt agctctaaac tgttaacata gaatgttact tggaaaaagt ctggaatatg    3534
tggtgtacac aagcagtgct tcgtgaatga gtttcttagc ttttatagtg cgccatgttt    3594
ctcaaagttt gttttgttg acaaaacatt ttataatata tatcttatgt ttatttttt    3654
tctcaactaa ttgtgtactg cactgtaagg tgaaaattag ccatccatta tttatcttct    3714
gtggcaatgc atttatatgg ttgattgggt ggggaatttt ttgcagaaag atgcaaagtg    3774
atgggttttc gacttcctat cgcagggagc ttttaagaaa tattaatttc ctatacattt    3834
ttccaatccc catgcaaact gttcctgttt acataccttc tctgttgtat cagtactttg    3894
agtgagaaga cagtttattt aaaacttgag caggctgttc agcatttttt ctgcttctga    3954
aatctgtata gtacactggt ttgtaatcat tatgtcttca ttgaaatcct tgctacttct    4014
cttcctcctc aatgaaatac attatatatt atctttatgt actcttaaga aaacgagca    4074
aggaagagta tcttcattat tctcattttc tctgagttgg aaacaaaaac atgaaggact    4134
ccaactagaa gacagatatt tacatttaaa tagattagtg ggaaaacttt aagagtttcc    4194
acatattagt tttcattttt tgagtcaaga gactgctcct tgtactggga gacactagta    4254
gtatatgtttt gtaatgttac tttaaaatta tcttttatt ttataaggcc cataaatact    4314
ggttaaactc tgttaaaagt gggccttcta tcttggatgg tttcactgcc atcagccatg    4374
ctgatatatt agaaatggca tccctatcta cttactttaa tgcttaaaat tatacataaa    4434
atgctttatt tagaaaacct acatgataca gtggtgtcag ccttgccatg tatcagtttc    4494
acttgaaatt tgagaccaat taaatttcaa ctgtttaggg tggagaaaga ggtactgaaa    4554
aacatgcaga tgaggatatc ttttatgtgc aacagtatcc tttgcatggg aggagagtta    4614
ctcttgaaag gcaggcagct taagtggaca atgttttgta tatagttgag aattttacga    4674
cacttttaaa aattgtgtaa ttgttaaatg tccagttttg ctctgttttg cctgaagttt    4734
tagtatttgt tttctaggtg gacctctgaa aaccaaacca gtacctgggg aggttagatg    4794
tgtgtttcag gcttggagtg tatgagtggt tttgcttgta ttttcctcca gagattttga    4854
actttaataa ttgcgtgtgt gttttttttt ttttaagtg gctttgtttt tttttctcaa    4914
gtaaaattgt gaacatattt cctttatagg ggcagggcat gagttaggga gactgaagag    4974
tattgtagac tgtacatgtg ccttcttaat gtgtttctcg acacattttt tttcagtaac    5034
ttgaaaattc aaaagggaca tttggttagg ttactgtaca tcaatctatg cataaatggc    5094
```

```
agcttgtttt cttgagccac ggtctaaatt ttgtttttat agaaattttt tatactgatt    5154
ggttcataga tggtcagttt tgtacacaga ctgaacaata cagcactttg ccaaaaatga    5214
gtgtagcatt gtttaaacat tgtgtgttaa cacctgttct ttgtaattgg gttgtggtgc    5274
attttgcact acctggagtt acagttttca atctgtcagt aaataaagtg tcctttaact    5334
tcaaaaaaaa aaaaaaa                                                   5351
```

<210> SEQ ID NO 4
<211> LENGTH: 164
<212> TYPE: PRT
<213> ORGANISM: Homo sapiens

<400> SEQUENCE: 4

```
Met Phe Gln Arg Leu Asn Lys Met Phe Val Gly Glu Val Ser Ser Ser
 1               5                  10                  15

Ser Asn Gln Glu Pro Glu Phe Asn Glu Lys Glu Asp Asp Glu Trp Ile
             20                  25                  30

Leu Val Asp Phe Ile Asp Thr Cys Thr Gly Phe Ser Ala Glu Glu Glu
         35                  40                  45

Glu Glu Glu Glu Asp Ile Ser Glu Glu Ser Pro Thr Glu His Pro Ser
     50                  55                  60

Val Phe Ser Cys Leu Pro Ala Ser Leu Glu Cys Leu Ala Asp Thr Ser
 65                  70                  75                  80

Asp Ser Cys Phe Leu Gln Phe Glu Ser Cys Pro Met Glu Glu Ser Trp
                 85                  90                  95

Phe Ile Thr Pro Pro Cys Phe Thr Ala Gly Gly Leu Thr Thr Ile
            100                 105                 110

Lys Val Glu Thr Ser Pro Met Glu Asn Leu Leu Ile Glu His Pro Ser
            115                 120                 125

Met Ser Val Tyr Ala Val His Asn Ser Cys Pro Gly Leu Ser Glu Ala
        130                 135                 140

Thr Arg Gly Thr Asp Glu Leu His Ser Pro Ser Ser Pro Arg Ala Arg
145                 150                 155                 160

Lys Ser Cys Leu
```

<210> SEQ ID NO 5
<211> LENGTH: 17518
<212> TYPE: DNA
<213> ORGANISM: Homo sapiens
<220> FEATURE:
<223> OTHER INFORMATION: /DEFINITION=Homo sapiens p53DINP1 gene for
      p53DINP1a, p53DINP1b, complete cds, alternative
      splicing.
<220> FEATURE:
<221> NAME/KEY: exon
<222> LOCATION: (2462)..(2612)
<223> OTHER INFORMATION: /gene="p53DINP1"
      /number=1
<220> FEATURE:
<221> NAME/KEY: exon
<222> LOCATION: (3215)..(3575)
<223> OTHER INFORMATION: /gene="p53DINP1"
      /number=2
<220> FEATURE:
<221> NAME/KEY: exon
<222> LOCATION: (11340)..(11377)
<223> OTHER INFORMATION: /gene="p53DINP1"
      /number=3
<220> FEATURE:
<221> NAME/KEY: exon
<222> LOCATION: (12718)..(17518)
<223> OTHER INFORMATION: /gene="p53DINP1"
      /number=4

```
-continued

<220> FEATURE:
<221> NAME/KEY: misc_feature
<222> LOCATION: (489)
<223> OTHER INFORMATION: n= A, T, C, or G
<220> FEATURE:
<221> NAME/KEY: misc_feature
<222> LOCATION: (2616)
<223> OTHER INFORMATION: n= A, T, C, or G
<220> FEATURE:
<221> NAME/KEY: misc_feature
<222> LOCATION: (2625)
<223> OTHER INFORMATION: n= A, T, C, or G
<220> FEATURE:
<221> NAME/KEY: misc_feature
<222> LOCATION: (2633)
<223> OTHER INFORMATION: n= A, T, C, or G
<220> FEATURE:
<221> NAME/KEY: misc_feature
<222> LOCATION: (2640)
<223> OTHER INFORMATION: n= A, T, C, or G
<220> FEATURE:
<221> NAME/KEY: misc_feature
<222> LOCATION: (2643)
<223> OTHER INFORMATION: n= A, T, C, or G
<220> FEATURE:
<221> NAME/KEY: misc_feature
<222> LOCATION: (2646)
<223> OTHER INFORMATION: n= A, T, C, or G
<220> FEATURE:
<221> NAME/KEY: misc_feature
<222> LOCATION: (2669)
<223> OTHER INFORMATION: n= A, T, C, or G
<220> FEATURE:
<221> NAME/KEY: misc_feature
<222> LOCATION: (2675)
<223> OTHER INFORMATION: n= A, T, C, or G
<220> FEATURE:
<221> NAME/KEY: misc_feature
<222> LOCATION: (2680)
<223> OTHER INFORMATION: n= A, T, C, or G
<220> FEATURE:
<221> NAME/KEY: misc_feature
<222> LOCATION: (2686)
<223> OTHER INFORMATION: n= A, T, C, or G
<220> FEATURE:
<221> NAME/KEY: misc_feature
<222> LOCATION: (2710)
<223> OTHER INFORMATION: n= A, T, C, or G
<220> FEATURE:
<221> NAME/KEY: misc_feature
<222> LOCATION: (2713)
<223> OTHER INFORMATION: n= A, T, C, or G
<220> FEATURE:
<221> NAME/KEY: misc_feature
<222> LOCATION: (3767)
<223> OTHER INFORMATION: n= A, T, C, or G
<220> FEATURE:
<221> NAME/KEY: misc_feature
<222> LOCATION: (4128)
<223> OTHER INFORMATION: n= A, T, C, or G
<220> FEATURE:
<221> NAME/KEY: misc_feature
<222> LOCATION: (4154)
<223> OTHER INFORMATION: n= A, T, C, or G
<220> FEATURE:
<221> NAME/KEY: misc_feature
<222> LOCATION: (4207)
<223> OTHER INFORMATION: n= A, T, C, or G
<220> FEATURE:
<221> NAME/KEY: misc_feature
<222> LOCATION: (4216)
<223> OTHER INFORMATION: n= A, T, C, or G
<220> FEATURE:
<221> NAME/KEY: misc_feature
<222> LOCATION: (4240)
<223> OTHER INFORMATION: n= A, T, C, or G
<220> FEATURE:
<221> NAME/KEY: misc_feature
<222> LOCATION: (4249)
```

```
<223> OTHER INFORMATION: n= A, T, C, or G
<220> FEATURE:
<221> NAME/KEY: misc_feature
<222> LOCATION: (4272)
<223> OTHER INFORMATION: n= A, T, C, or G
<220> FEATURE:
<221> NAME/KEY: misc_feature
<222> LOCATION: (4308)
<223> OTHER INFORMATION: n= A, T, C, or G
<220> FEATURE:
<221> NAME/KEY: misc_feature
<222> LOCATION: (4345)
<223> OTHER INFORMATION: n= A, T, C, or G
<220> FEATURE:
<221> NAME/KEY: misc_feature
<222> LOCATION: (4360)
<223> OTHER INFORMATION: n= A, T, C, or G
<220> FEATURE:
<221> NAME/KEY: misc_feature
<222> LOCATION: (4367)
<223> OTHER INFORMATION: n= A, T, C, or G
<220> FEATURE:
<221> NAME/KEY: misc_feature
<222> LOCATION: (4380)
<223> OTHER INFORMATION: n= A, T, C, or G
<220> FEATURE:
<221> NAME/KEY: misc_feature
<222> LOCATION: (4385)
<223> OTHER INFORMATION: n= A, T, C, or G
<220> FEATURE:
<221> NAME/KEY: misc_feature
<222> LOCATION: (4418)
<223> OTHER INFORMATION: n= A, T, C, or G
<220> FEATURE:
<221> NAME/KEY: misc_feature
<222> LOCATION: (4460)
<223> OTHER INFORMATION: n= A, T, C, or G
<220> FEATURE:
<221> NAME/KEY: misc_feature
<222> LOCATION: (4470)
<223> OTHER INFORMATION: n= A, T, C, or G
<220> FEATURE:
<221> NAME/KEY: misc_feature
<222> LOCATION: (4617)
<223> OTHER INFORMATION: n= A, T, C, or G
<220> FEATURE:
<221> NAME/KEY: misc_feature
<222> LOCATION: (4629)
<223> OTHER INFORMATION: n= A, T, C, or G
<220> FEATURE:
<221> NAME/KEY: misc_feature
<222> LOCATION: (4653)
<223> OTHER INFORMATION: n= A, T, C, or G
<220> FEATURE:
<221> NAME/KEY: misc_feature
<222> LOCATION: (4743)
<223> OTHER INFORMATION: n= A, T, C, or G
<220> FEATURE:
<221> NAME/KEY: misc_feature
<222> LOCATION: (4768)
<223> OTHER INFORMATION: n= A, T, C, or G
<220> FEATURE:
<221> NAME/KEY: misc_feature
<222> LOCATION: (4789)
<223> OTHER INFORMATION: n= A, T, C, or G
<220> FEATURE:
<221> NAME/KEY: misc_feature
<222> LOCATION: (4795)
<223> OTHER INFORMATION: n= A, T, C, or G
<220> FEATURE:
<221> NAME/KEY: misc_feature
<222> LOCATION: (4856)
<223> OTHER INFORMATION: n= A, T, C, or G
<220> FEATURE:
<221> NAME/KEY: misc_feature
<222> LOCATION: (4877)
<223> OTHER INFORMATION: n= A, T, C, or G
<220> FEATURE:
<221> NAME/KEY: misc_feature
```

```
<222> LOCATION: (4882)
<223> OTHER INFORMATION: n= A, T, C, or G
<220> FEATURE:
<221> NAME/KEY: misc_feature
<222> LOCATION: (4892)
<223> OTHER INFORMATION: n= A, T, C, or G
<220> FEATURE:
<221> NAME/KEY: misc_feature
<222> LOCATION: (4939)
<223> OTHER INFORMATION: n= A, T, C, or G
<220> FEATURE:
<221> NAME/KEY: misc_feature
<222> LOCATION: (5319)
<223> OTHER INFORMATION: n= A, T, C, or G
<220> FEATURE:
<221> NAME/KEY: misc_feature
<222> LOCATION: (5344)
<223> OTHER INFORMATION: n= A, T, C, or G
<220> FEATURE:
<221> NAME/KEY: misc_feature
<222> LOCATION: (5453)
<223> OTHER INFORMATION: n= A, T, C, or G
<220> FEATURE:
<221> NAME/KEY: misc_feature
<222> LOCATION: (5468)
<223> OTHER INFORMATION: n= A, T, C, or G
<220> FEATURE:
<221> NAME/KEY: misc_feature
<222> LOCATION: (5485)
<223> OTHER INFORMATION: n= A, T, C, or G
<220> FEATURE:
<221> NAME/KEY: misc_feature
<222> LOCATION: (5625)
<223> OTHER INFORMATION: n= A, T, C, or G
<220> FEATURE:
<221> NAME/KEY: misc_feature
<222> LOCATION: (5659)
<223> OTHER INFORMATION: n= A, T, C, or G
<220> FEATURE:
<221> NAME/KEY: misc_feature
<222> LOCATION: (5748)
<223> OTHER INFORMATION: n= A, T, C, or G
<220> FEATURE:
<221> NAME/KEY: misc_feature
<222> LOCATION: (5760)
<223> OTHER INFORMATION: n= A, T, C, or G
<220> FEATURE:
<221> NAME/KEY: misc_feature
<222> LOCATION: (5780)
<223> OTHER INFORMATION: n= A, T, C, or G
<220> FEATURE:
<221> NAME/KEY: misc_feature
<222> LOCATION: (5794)
<223> OTHER INFORMATION: n= A, T, C, or G
<220> FEATURE:
<221> NAME/KEY: misc_feature
<222> LOCATION: (5814)
<223> OTHER INFORMATION: n= A, T, C, or G
<220> FEATURE:
<221> NAME/KEY: misc_feature
<222> LOCATION: (5832)
<223> OTHER INFORMATION: n= A, T, C, or G
<220> FEATURE:
<221> NAME/KEY: misc_feature
<222> LOCATION: (5863)
<223> OTHER INFORMATION: n= A, T, C, or G
<220> FEATURE:
<221> NAME/KEY: misc_feature
<222> LOCATION: (5872)
<223> OTHER INFORMATION: n= A, T, C, or G
<220> FEATURE:
<221> NAME/KEY: misc_feature
<222> LOCATION: (5908)
<223> OTHER INFORMATION: n= A, T, C, or G
<220> FEATURE:
<221> NAME/KEY: misc_feature
<222> LOCATION: (5916)
<223> OTHER INFORMATION: n= A, T, C, or G
<220> FEATURE:
```

```
<221> NAME/KEY: misc_feature
<222> LOCATION: (5948)
<223> OTHER INFORMATION: n= A, T, C, or G
<220> FEATURE:
<221> NAME/KEY: misc_feature
<222> LOCATION: (5963)
<223> OTHER INFORMATION: n= A, T, C, or G
<220> FEATURE:
<221> NAME/KEY: misc_feature
<222> LOCATION: (5999)
<223> OTHER INFORMATION: n= A, T, C, or G
<220> FEATURE:
<221> NAME/KEY: misc_feature
<222> LOCATION: (6017)
<223> OTHER INFORMATION: n= A, T, C, or G
<220> FEATURE:
<221> NAME/KEY: misc_feature
<222> LOCATION: (6029)
<223> OTHER INFORMATION: n= A, T, C, or G
<220> FEATURE:
<221> NAME/KEY: misc_feature
<222> LOCATION: (6074)
<223> OTHER INFORMATION: n= A, T, C, or G
<220> FEATURE:
<221> NAME/KEY: misc_feature
<222> LOCATION: (6157)
<223> OTHER INFORMATION: n= A, T, C, or G
<220> FEATURE:
<221> NAME/KEY: misc_feature
<222> LOCATION: (6183)
<223> OTHER INFORMATION: n= A, T, C, or G
<220> FEATURE:
<221> NAME/KEY: misc_feature
<222> LOCATION: (6188)
<223> OTHER INFORMATION: n= A, T, C, or G
<220> FEATURE:
<221> NAME/KEY: misc_feature
<222> LOCATION: (6193)
<223> OTHER INFORMATION: n= A, T, C, or G
<220> FEATURE:
<221> NAME/KEY: misc_feature
<222> LOCATION: (6235)
<223> OTHER INFORMATION: n= A, T, C, or G
<220> FEATURE:
<221> NAME/KEY: misc_feature
<222> LOCATION: (6290)
<223> OTHER INFORMATION: n= A, T, C, or G
<220> FEATURE:
<221> NAME/KEY: misc_feature
<222> LOCATION: (6327)
<223> OTHER INFORMATION: n= A, T, C, or G
<220> FEATURE:
<221> NAME/KEY: misc_feature
<222> LOCATION: (6694)
<223> OTHER INFORMATION: n= A, T, C, or G
<220> FEATURE:
<221> NAME/KEY: misc_feature
<222> LOCATION: (6784)
<223> OTHER INFORMATION: n= A, T, C, or G
<220> FEATURE:
<221> NAME/KEY: misc_feature
<222> LOCATION: (6825)
<223> OTHER INFORMATION: n= A, T, C, or G
<220> FEATURE:
<221> NAME/KEY: misc_feature
<222> LOCATION: (6839)
<223> OTHER INFORMATION: n= A, T, C, or G
<220> FEATURE:
<221> NAME/KEY: misc_feature
<222> LOCATION: (6878)
<223> OTHER INFORMATION: n= A, T, C, or G
<220> FEATURE:
<221> NAME/KEY: misc_feature
<222> LOCATION: (6898)
<223> OTHER INFORMATION: n= A, T, C, or G
<220> FEATURE:
<221> NAME/KEY: misc_feature
<222> LOCATION: (6903)
<223> OTHER INFORMATION: n= A, T, C, or G
```

```
<220> FEATURE:
<221> NAME/KEY: misc_feature
<222> LOCATION: (6906)
<223> OTHER INFORMATION: n= A, T, C, or G
<220> FEATURE:
<221> NAME/KEY: misc_feature
<222> LOCATION: (7020)
<223> OTHER INFORMATION: n= A, T, C, or G
<220> FEATURE:
<221> NAME/KEY: misc_feature
<222> LOCATION: (7022)
<223> OTHER INFORMATION: n= A, T, C, or G
<220> FEATURE:
<221> NAME/KEY: misc_feature
<222> LOCATION: (7064)
<223> OTHER INFORMATION: n= A, T, C, or G
<220> FEATURE:
<221> NAME/KEY: misc_feature
<222> LOCATION: (7084)
<223> OTHER INFORMATION: n= A, T, C, or G
<220> FEATURE:
<221> NAME/KEY: misc_feature
<222> LOCATION: (7240)
<223> OTHER INFORMATION: n= A, T, C, or G
<220> FEATURE:
<221> NAME/KEY: misc_feature
<222> LOCATION: (7295)
<223> OTHER INFORMATION: n= A, T, C, or G
<220> FEATURE:
<221> NAME/KEY: misc_feature
<222> LOCATION: (7299)
<223> OTHER INFORMATION: n= A, T, C, or G
<220> FEATURE:
<221> NAME/KEY: misc_feature
<222> LOCATION: (7339)
<223> OTHER INFORMATION: n= A, T, C, or G
<220> FEATURE:
<221> NAME/KEY: misc_feature
<222> LOCATION: (7341)
<223> OTHER INFORMATION: n= A, T, C, or G
<220> FEATURE:
<221> NAME/KEY: misc_feature
<222> LOCATION: (7355)
<223> OTHER INFORMATION: n= A, T, C, or G
<220> FEATURE:
<221> NAME/KEY: misc_feature
<222> LOCATION: (7553)
<223> OTHER INFORMATION: n= A, T, C, or G
<220> FEATURE:
<221> NAME/KEY: misc_feature
<222> LOCATION: (7557)
<223> OTHER INFORMATION: n= A, T, C, or G
<220> FEATURE:
<221> NAME/KEY: misc_feature
<222> LOCATION: (7745)
<223> OTHER INFORMATION: n= A, T, C, or G
<220> FEATURE:
<221> NAME/KEY: misc_feature
<222> LOCATION: (7767)
<223> OTHER INFORMATION: n= A, T, C, or G
<220> FEATURE:
<221> NAME/KEY: misc_feature
<222> LOCATION: (7770)
<223> OTHER INFORMATION: n= A, T, C, or G
<220> FEATURE:
<221> NAME/KEY: misc_feature
<222> LOCATION: (7816)
<223> OTHER INFORMATION: n= A, T, C, or G
<220> FEATURE:
<221> NAME/KEY: misc_feature
<222> LOCATION: (7822)
<223> OTHER INFORMATION: n= A, T, C, or G
<220> FEATURE:
<221> NAME/KEY: misc_feature
<222> LOCATION: (7838)..(7839)
<223> OTHER INFORMATION: n= A, T, C, or G
<220> FEATURE:
<221> NAME/KEY: misc_feature
<222> LOCATION: (7856)
```

```
<223> OTHER INFORMATION: n= A, T, C, or G
<220> FEATURE:
<221> NAME/KEY: misc_feature
<222> LOCATION: (7888)
<223> OTHER INFORMATION: n= A, T, C, or G
<220> FEATURE:
<221> NAME/KEY: misc_feature
<222> LOCATION: (8001)
<223> OTHER INFORMATION: n= A, T, C, or G
<220> FEATURE:
<221> NAME/KEY: misc_feature
<222> LOCATION: (8026)
<223> OTHER INFORMATION: n= A, T, C, or G
<220> FEATURE:
<221> NAME/KEY: misc_feature
<222> LOCATION: (8071)
<223> OTHER INFORMATION: n= A, T, C, or G
<220> FEATURE:
<221> NAME/KEY: misc_feature
<222> LOCATION: (8096)
<223> OTHER INFORMATION: n= A, T, C, or G
<220> FEATURE:
<221> NAME/KEY: misc_feature
<222> LOCATION: (8106)
<223> OTHER INFORMATION: n= A, T, C, or G
<220> FEATURE:
<221> NAME/KEY: misc_feature
<222> LOCATION: (8111)
<223> OTHER INFORMATION: n= A, T, C, or G
<220> FEATURE:
<221> NAME/KEY: misc_feature
<222> LOCATION: (8124)
<223> OTHER INFORMATION: n= A, T, C, or G
<220> FEATURE:
<221> NAME/KEY: misc_feature
<222> LOCATION: (8128)
<223> OTHER INFORMATION: n= A, T, C, or G
<220> FEATURE:
<221> NAME/KEY: misc_feature
<222> LOCATION: (8130)
<223> OTHER INFORMATION: n= A, T, C, or G
<220> FEATURE:
<221> NAME/KEY: misc_feature
<222> LOCATION: (8160)
<223> OTHER INFORMATION: n= A, T, C, or G
<220> FEATURE:
<221> NAME/KEY: misc_feature
<222> LOCATION: (8170)
<223> OTHER INFORMATION: n= A, T, C, or G
<220> FEATURE:
<221> NAME/KEY: misc_feature
<222> LOCATION: (8178)
<223> OTHER INFORMATION: n= A, T, C, or G
<220> FEATURE:
<221> NAME/KEY: misc_feature
<222> LOCATION: (8196)
<223> OTHER INFORMATION: n= A, T, C, or G
<220> FEATURE:
<221> NAME/KEY: misc_feature
<222> LOCATION: (8200)
<223> OTHER INFORMATION: n= A, T, C, or G
<220> FEATURE:
<221> NAME/KEY: misc_feature
<222> LOCATION: (8214)
<223> OTHER INFORMATION: n= A, T, C, or G
<220> FEATURE:
<221> NAME/KEY: misc_feature
<222> LOCATION: (8231)
<223> OTHER INFORMATION: n= A, T, C, or G
<220> FEATURE:
<221> NAME/KEY: misc_feature
<222> LOCATION: (8244)
<223> OTHER INFORMATION: n= A, T, C, or G
<220> FEATURE:
<221> NAME/KEY: misc_feature
<222> LOCATION: (8566)
<223> OTHER INFORMATION: n= A, T, C, or G
<220> FEATURE:
<221> NAME/KEY: misc_feature
```

-continued

```
<222> LOCATION: (8611)
<223> OTHER INFORMATION: n= A, T, C, or G
<220> FEATURE:
<221> NAME/KEY: misc_feature
<222> LOCATION: (8662)
<223> OTHER INFORMATION: n= A, T, C, or G
<220> FEATURE:
<221> NAME/KEY: misc_feature
<222> LOCATION: (8763)
<223> OTHER INFORMATION: n= A, T, C, or G
<220> FEATURE:
<221> NAME/KEY: misc_feature
<222> LOCATION: (8768)
<223> OTHER INFORMATION: n= A, T, C, or G
<220> FEATURE:
<221> NAME/KEY: misc_feature
<222> LOCATION: (9000)
<223> OTHER INFORMATION: n= A, T, C, or G
<220> FEATURE:
<221> NAME/KEY: misc_feature
<222> LOCATION: (9014)
<223> OTHER INFORMATION: n= A, T, C, or G
<220> FEATURE:
<221> NAME/KEY: misc_feature
<222> LOCATION: (9028)
<223> OTHER INFORMATION: n= A, T, C, or G
<220> FEATURE:
<221> NAME/KEY: misc_feature
<222> LOCATION: (9043)
<223> OTHER INFORMATION: n= A, T, C, or G
<220> FEATURE:
<221> NAME/KEY: misc_feature
<222> LOCATION: (9240)
<223> OTHER INFORMATION: n= A, T, C, or G
<220> FEATURE:
<221> NAME/KEY: misc_feature
<222> LOCATION: (9242)
<223> OTHER INFORMATION: n= A, T, C, or G
<220> FEATURE:
<221> NAME/KEY: misc_feature
<222> LOCATION: (9245)
<223> OTHER INFORMATION: n= A, T, C, or G
<220> FEATURE:
<221> NAME/KEY: misc_feature
<222> LOCATION: (9264)
<223> OTHER INFORMATION: n= A, T, C, or G
<220> FEATURE:
<221> NAME/KEY: misc_feature
<222> LOCATION: (9279)
<223> OTHER INFORMATION: n= A, T, C, or G
<220> FEATURE:
<221> NAME/KEY: misc_feature
<222> LOCATION: (9371)
<223> OTHER INFORMATION: n= A, T, C, or G
<220> FEATURE:
<221> NAME/KEY: misc_feature
<222> LOCATION: (9373)
<223> OTHER INFORMATION: n= A, T, C, or G
<220> FEATURE:
<221> NAME/KEY: misc_feature
<222> LOCATION: (9377)
<223> OTHER INFORMATION: n= A, T, C, or G
<220> FEATURE:
<221> NAME/KEY: misc_feature
<222> LOCATION: (9384)
<223> OTHER INFORMATION: n= A, T, C, or G
<220> FEATURE:
<221> NAME/KEY: misc_feature
<222> LOCATION: (10005)
<223> OTHER INFORMATION: n= A, T, C, or G
<220> FEATURE:
<221> NAME/KEY: misc_feature
<222> LOCATION: (10244)
<223> OTHER INFORMATION: n= A, T, C, or G
<220> FEATURE:
<221> NAME/KEY: misc_feature
<222> LOCATION: (10303)
<223> OTHER INFORMATION: n= A, T, C, or G
<220> FEATURE:
```

-continued

```
<221> NAME/KEY: misc_feature
<222> LOCATION: (10506)
<223> OTHER INFORMATION: n= A, T, C, or G
<220> FEATURE:
<221> NAME/KEY: misc_feature
<222> LOCATION: (10844)
<223> OTHER INFORMATION: n= A, T, C, or G
<220> FEATURE:
<221> NAME/KEY: misc_feature
<222> LOCATION: (10850)
<223> OTHER INFORMATION: n= A, T, C, or G
<220> FEATURE:
<221> NAME/KEY: misc_feature
<222> LOCATION: (10858)
<223> OTHER INFORMATION: n= A, T, C, or G
<220> FEATURE:
<221> NAME/KEY: misc_feature
<222> LOCATION: (10862)
<223> OTHER INFORMATION: n= A, T, C, or G
<220> FEATURE:
<221> NAME/KEY: misc_feature
<222> LOCATION: (10874)
<223> OTHER INFORMATION: n= A, T, C, or G
<220> FEATURE:
<221> NAME/KEY: misc_feature
<222> LOCATION: (10898)
<223> OTHER INFORMATION: n= A, T, C, or G
<220> FEATURE:
<221> NAME/KEY: misc_feature
<222> LOCATION: (11012)
<223> OTHER INFORMATION: n= A, T, C, or G
<220> FEATURE:
<221> NAME/KEY: misc_feature
<222> LOCATION: (11019)
<223> OTHER INFORMATION: n= A, T, C, or G
<220> FEATURE:
<221> NAME/KEY: misc_feature
<222> LOCATION: (11478)
<223> OTHER INFORMATION: n= A, T, C, or G
<220> FEATURE:
<221> NAME/KEY: misc_feature
<222> LOCATION: (11484)
<223> OTHER INFORMATION: n= A, T, C, or G
<220> FEATURE:
<221> NAME/KEY: misc_feature
<222> LOCATION: (11509)
<223> OTHER INFORMATION: n= A, T, C, or G
<220> FEATURE:
<221> NAME/KEY: misc_feature
<222> LOCATION: (11559)
<223> OTHER INFORMATION: n= A, T, C, or G
<220> FEATURE:
<221> NAME/KEY: misc_feature
<222> LOCATION: (11585)
<223> OTHER INFORMATION: n= A, T, C, or G
<220> FEATURE:
<221> NAME/KEY: misc_feature
<222> LOCATION: (11669)
<223> OTHER INFORMATION: n= A, T, C, or G
<220> FEATURE:
<221> NAME/KEY: misc_feature
<222> LOCATION: (11690)
<223> OTHER INFORMATION: n= A, T, C, or G
<220> FEATURE:
<221> NAME/KEY: misc_feature
<222> LOCATION: (11718)
<223> OTHER INFORMATION: n= A, T, C, or G
<220> FEATURE:
<221> NAME/KEY: misc_feature
<222> LOCATION: (11735)
<223> OTHER INFORMATION: n= A, T, C, or G
<220> FEATURE:
<221> NAME/KEY: misc_feature
<222> LOCATION: (11739)
<223> OTHER INFORMATION: n= A, T, C, or G
<220> FEATURE:
<221> NAME/KEY: misc_feature
<222> LOCATION: (11776)
<223> OTHER INFORMATION: n= A, T, C, or G
```

```
<220> FEATURE:
<221> NAME/KEY: misc_feature
<222> LOCATION: (11792)
<223> OTHER INFORMATION: n= A, T, C, or G
<220> FEATURE:
<221> NAME/KEY: misc_feature
<222> LOCATION: (11817)
<223> OTHER INFORMATION: n= A, T, C, or G
<220> FEATURE:
<221> NAME/KEY: misc_feature
<222> LOCATION: (12063)
<223> OTHER INFORMATION: n= A, T, C, or G
<220> FEATURE:
<221> NAME/KEY: misc_feature
<222> LOCATION: (12307)
<223> OTHER INFORMATION: n= A, T, C, or G
<220> FEATURE:
<221> NAME/KEY: misc_feature
<222> LOCATION: (12402)
<223> OTHER INFORMATION: n= A, T, C, or G
<220> FEATURE:
<221> NAME/KEY: misc_feature
<222> LOCATION: (12563)
<223> OTHER INFORMATION: n= A, T, C, or G
<220> FEATURE:
<221> NAME/KEY: misc_feature
<222> LOCATION: (12565)..(12566)
<223> OTHER INFORMATION: n= A, T, C, or G
<220> FEATURE:
<221> NAME/KEY: misc_feature
<222> LOCATION: (12586)
<223> OTHER INFORMATION: n= A, T, C, or G
<220> FEATURE:
<221> NAME/KEY: misc_feature
<222> LOCATION: (12599)
<223> OTHER INFORMATION: n= A, T, C, or G
<220> FEATURE:
<221> NAME/KEY: misc_feature
<222> LOCATION: (12603)
<223> OTHER INFORMATION: n= A, T, C, or G
<220> FEATURE:
<221> NAME/KEY: misc_feature
<222> LOCATION: (12607)
<223> OTHER INFORMATION: n= A, T, C, or G
<220> FEATURE:
<221> NAME/KEY: misc_feature
<222> LOCATION: (12611)
<223> OTHER INFORMATION: n= A, T, C, or G
<220> FEATURE:
<221> NAME/KEY: misc_feature
<222> LOCATION: (12625)
<223> OTHER INFORMATION: n= A, T, C, or G
<220> FEATURE:
<221> NAME/KEY: misc_feature
<222> LOCATION: (12629)
<223> OTHER INFORMATION: n= A, T, C, or G
<220> FEATURE:
<221> NAME/KEY: misc_feature
<222> LOCATION: (12646)
<223> OTHER INFORMATION: n= A, T, C, or G
<220> FEATURE:
<221> NAME/KEY: misc_feature
<222> LOCATION: (12679)
<223> OTHER INFORMATION: n= A, T, C, or G
<220> FEATURE:
<221> NAME/KEY: misc_feature
<222> LOCATION: (12692)
<223> OTHER INFORMATION: n= A, T, C, or G
<220> FEATURE:
<221> NAME/KEY: misc_feature
<222> LOCATION: (12706)
<223> OTHER INFORMATION: n= A, T, C, or G
<220> FEATURE:
<221> NAME/KEY: misc_feature
<222> LOCATION: (13896)
<223> OTHER INFORMATION: n= A, T, C, or G

<400> SEQUENCE: 5
```

-continued

```
tcatagctta ctgcatcctt gaacctggat tcaagagatc ctcccacgtc agcctcccaa      60
gtagctagga ctacaggtgc acaccactgt acctggctaa ttttttaaaa ttttttttgta    120 gaaacaggtt attttgttgc ctaggctggt ctccaactcc taggctcaag cattcctgtg    180
gcctcagcct cccaaaatgc taggattgca gacatgagcc tccacaccta gcctcatcca    240
ttcctatgct ttttatcact gtctttgtgt catcagctcc caaatctatg ccctagctg     300 agaccacact cctgagctcc aaagctctat atcctgctgc ctgctggaca tctccaactg    360
cattattttg catatccccc caatttacca tattcgaaat gcctaacctg tactttctgc    420
aggattcatt cctgtttccc taaatggttc caccatcctc tcagttggcc aagccagaaa    480
catggggtnt gagactttc cccttcccct cttccaggct taacaaggcc ctgcaggacc     540
tgttcctgct cagctcccct agcctgctat tgcgaccctc cctctggacc ttgagcggta    600
ctgaaggtgc acattctca ctcatccaca gggttccata gtgttcattt gcccccttcc    660
tccagcactg acctcagcca ctcaagagta aagtcattgc aggagtccac acaggtagcc    720
tggagaacac caaatacttc ttccatggca ttcatcacac cggattgtta aatttgtggg    780
agggccctgt tcacagccat ctcccctgtg cccagcaatg cacctgatgc ataacaggtg    840
ctcagtaaat acatgtagaa taatagttga cctggactga ggactttatt cgaagtattt    900
tgctaagtcc atcgccttta acaagagtag gatcagggag actgtctagt agacagtttt    960
ggcaaagtct cagagacaac agtttggctt aaactaggat gagagtggtg gatggaagca   1020
ggcagattcg agctgcctgt gctcctgggg ttgacgggac ttggtggttg ggatgagggg   1080
tgagtaggag ggagcaaaag gcatgcgggt gcggcagctc acgcctgtaa tcctagcatt   1140
ttgggaggct gaggtgggcg gatcatgagg tcaggagatc gagaccatcc tggctaacat   1200
ggtgaaaccc tgtctccact aaataaaaaa aaaagaaatt agccggatgt ggtggtgggc   1260
gcctgtagtc ccagctactt gggaggctga ggcaggagaa tggcgtgaac ccgggaggca   1320
gagcttggaa tgagccaaga tcgcctcact gcatgcactc cagcctgggc aacagacaaa   1380
gactccgtct caaaaaaaaa aaagcgtgaa gggtgactgc tagggtgttg gcctgaataa   1440
ctgccagctg ctgctgcttc ctgagaaagg gatgaagggc agtgtatatg aataagtttg   1500
tgggggtaaa aaacctatct ttggtatgtg tttggtttga tacgcccatc aggtagccag   1560
gtagaaatgg ataaatattc caagatcaag caagcgtgga gttttttcatt tagaactcac   1620 cagaattccg taaggtagga gctgttgcca gctgaagtca cataacttcc taactcacac   1680
agcaagtgag cagctagcca gggtttgaat gcaggtggct gacccagcac ccacctgctg    1740
agctgctaca caggaagggt gtttccagtt ctaggtttgg ccaagctcag tttcctacag    1800
tgtaaatttc ttcatgccag ctgtaggaat tgtttagaag gtcaaagtat gcttgctggg    1860
cttacagatt ttaagtgtaa tcaggtgtgc ttacagttat agacaagaag tacagagtag    1920
aagagaaaat gagccagagg aggatgaggg cctggcataa tggtggtcac caggcactgt    1980
tgctgggact tctgagcagt tgaataacat atagcaagac tgttactatc tagaatttgc    2040
tcatctgctt gcagaaaagt ttgaaggata ttattcaaat tcaccttatt ataaaagcat    2100
aaatatgaaa agaaccaac tctttccctt ttatttcaca ttttaagata tttataggtt    2160
gaatttgagt aagagtattt acaaaacatt atgttgcatt tcttgtgttt gactcctgca    2220
gaaagggaat agctgtagaa tgtaggccaa ggcatatgct ttcttctaag ggtatgtgtg    2280
tatgtgtatg tacttatgta tatatgtgca tgctgatttg aaataacttc ctttttctgt    2340 tttatttag gtacaatgac tcttcttgct tttcacctaa gttgaataag caccctgtgc    2400
```

```
actttaatct cctgtcggta ccattgggcc aactaaagac aaggttttga aatctcagct    2460
ataaaagaca tccagccaaa ctctcagtct tgccttaaca atgttccaga ggctgaataa    2520
aatgtttgtg ggtgaagtca gttcttcctc caaccaagaa ccagaattca atgagaaaga    2580
agatgatgaa tggattcttg ttgacttcat aggtanggta cactnggtta ctnggtggtn    2640
canctncaca gtaaaaatgg aaacttgcnt ctcanttttn gcatanggaa accaataact    2700 gagggotttn canccttgaa aatgaagcag gatttgtctt taaaaaattg caggaaacat    2760
ctgtgctaga taatgtcagt gaaattgact gacatcagac tttttagttt tgcaactctc    2820
acagattgat tagatcaagg gcacttcatt agaagcccct tttattagac aagtagtaac    2880
caatatgtct cattacatag ttatccagca gaatagaaac agtcttaaaa tcactcctgc    2940
aaagccaaca taaatctatc ccatatagtg acacacacac acacacacag aatttctgtg    3000
ctcagaaacc catttatagt catatagatg aatataaatg ggtttctgaa ctaaataaaa    3060
gaagatacgt gagcatcagc taatagtatc atctcttctt tttctgtgct gtgaatttga    3120
tgggtgactt tataatgact gcccaatgtg ataatcatcc tcctgtggga ctcttcaaca    3180
acacacgtgg actgcaatgt ggactacgat ctagatactt gcactggttt ctcagcagaa    3240
gaagaagaag aagaggagga catcagtgaa gagtcaccta ctgagcaccc ttcagtctttt   3300 tcctgtttac cggcatctct tgagtgcttg gctgatacaa gtgattcctg ctttctccag    3360
tttgagtcat gtccaatgga ggagagctgg tttatcaccc cacccccatg tttttactgca   3420 ggtggattaa ccactatcaa ggtggaaaca agtcctatgg aaaaccttct cattgaacat    3480
cccagcatgt ctgtctatgc tgtgcataac tcctgccctg gtctcagtga ggccacccgt    3540
gggactgatg aattacatag cccaagtagt cccaggtacg ttacaagtat ttaactctct    3600
gtaggcagtc cactgagcat gcattttgtc tctactgtaa ttcaaagcta agttattaga    3660
agatgcaaaa ctaattttgt tagagattta tgaaagcatg tgcatagtac acaagatggt    3720
ccgtaagata acttgttgac cacagtgtct cacacctgta atcccancac tttgggaggc    3780
caaggcaggc agatcactta agctcaggag ttcaagacca ccctgggcaa catggtgaaa    3840
ccccgtctgt ataaaaaata acaaaaaatt agccaggtgt ggtggtgcac acctgtagtc    3900
ccagctactc aggaggctga ggtgggagga tggcttgaac caggaggcag aggttgcatt    3960
gagtcaagat tgtgccactg cacatcagcc tgggtgacag agcaagactc tgtctcaaaa    4020
acaaaaactt gttcatttta gatttttta agaaagttag atgtagcatg gccccagtta    4080
tataatagca ttctcattta caaaattctg ctactgatta gaaataanac tggcatttct    4140
gttaagtatc ttanaacata actctgactt tatagactgg attatttacg gtatcaaatt    4200
caactanaat atcatntctt aaaatttatt ttcttccaan tatttctanc tacatctcat    4260
caaatgatgt anccttgaaa accttgtctg agaatttaac aaactcantt tcttcctgca    4320
atactcacac tgcacagtca cccantgctt ctgacaccan atgtgtnggt tttttccacn    4380
cccangcaaa cagtccccat cagtggacac cctctaantg tcctctgatt caattcaatt    4440
ctgacactgt ctacctccan attgcatctn aatccatagg ttaaaggctt agtcccaaaa    4500
gactgcctcc catttctgat gccaatctca agccccaggt tttacttatg cttctgacca    4560
accagctgta aactggtgtt cccatgaccc cttccttggg tttgattaat ttgctanaac    4620
atcttatana acttggggga acatgttac canttattata aaaaggatac agatgaaggg     4680
atgcataagg caaggcccat gccctctgtg caccccaccc tccgggaacc tccacatgtt    4740
```

```
canctctcca gaagctccct gaactcanta ctattggggt cttatggang catcngtaca    4800
taggcataat tgattaaatc attggccatt ggtgattggc ttaaccttca aacccnctcc    4860
cctctctgga atttganggg tngggctaaa antcccaact gttacttggt ctttatagtg    4920
accacatccc atcctgaanc tgcctaattg ctgccaacca ccagtcaact aattagcata    4980
cgctttccac attggaggtt ccaagggatt ttaggagttg tatgccagga aactgacaag    5040
accgaatata tattttacag tatcacagtc cagcctcagt cttcaaactt ggattactta    5100
caacaaaagg atatggaact caaaaaatac tggcacaaca ccagaatccc attcagtcag    5160
taattcattc catccatcat cgtactgtat gagcatgtct cccagggtga ggccactcag    5220
gtttgcaggt taattgatct tgttggtttc caaaaccaga atggttttta gcaaacacgt    5280
agcttcaccc tttcaggcat ctggtatacc tgagcttana acaatgtca tcttttctc      5340 tgancctgtt tcaaggtatt aatataatga attgatccca attcataacc tatttattca    5400
ttcttttgtc ttctttctct tcatttatac ccaaactttt ccatctctgg aanggacgtt    5460
agctttancc actgtgctgg tctanattgc aggtagcaat actagtttag caagtacctc    5520
tccctcagtc cactcccatt cagataqggt taggtgacat aggtacaaaa ttagtaggct    5580 gttttacca ccagacaata cagctgcatt cgttgttggc tccanttttg caagatgggg     5640
tctaggtaac cccataana cccttaggaa ttttgacata aggtttaaaa acatatttac     5700
agcttcttgc tcaggaacca tccctgcttc cagtacttgt agttacancc ctggtcctan    5760
gaccattgca tccagtacan gaaaaaaaaa tgangtgatg tgggaaacaa aaanttaaag    5820
tcattatact ancatactta acccttggct acaattgcat aantcatgcc ancatcctcc    5880
tccccatccc ttcttcctca gataccanaa aaacangaaa atcttgtggg gacatccaac    5940
ccttcatnct tttatccccc cantttgttt ttgggttttt ttttttttt gaaataaant     6000 ctcactgtgt cacccangct ggagtgcant ggcaggatct tggctcagcg caacctctgc    6060
ctcccgggtt caantgattc tcctttctca gcctcccaag tagctgggat tacaggcgcc    6120
cgccaccata cctgggtaat atttgtactt ttagtanaaa gggggtttca ccatatttgc    6180
cangctantc tcnaactcct gacctttggt gatccaccgc ctctgcctcc caaantgttt    6240
ttgggcatta tgggctgtat aatgtgtcct ttggtctgaa aaaatgacan ttaactatcc    6300
acatccaggc agtatcttct gttgtangtt ttttttggcac tctgagcatt tgcatcttcc    6360
attggttaag taaagcccac tccagagact gtcttttctt ctcaagaccc attttgtagc    6420
tccccaggac taccagcact agtctcactt gcagctatgc tcagggcctt cccaccaggg    6480
gaatctgccc ctcatcagta gtctgtctct tttgctggct ggcagaacgg ttctcattgg    6540
tatttgtgcc tgagagagta gaagaggaat gtctagatgc agcctgtctc tgcactgcct    6600
gtaccactca tttaatgaac ccaggatggc acctccaggg gagcacatgg agatatatct    6660
gcttccagtc ccagtcacct tccaaacctg gaanggagtt cttctgatgg ccactggcat    6720
gtcctaatat acccctcaaa tttccgtagg gttgtgctcc ctatggaagc catcccttta    6780
aaantccagg ttttcattgt gattctgcct gaccatgtcc actanccact gcccatgant    6840
cagtaaaaac caaacctagg ggcttccatc atcgctanga aaacagcgtg caattcancc    6900
ccncanaacc gaattgtttt taccttcttt gatcaaagta gcatccttcc aaacaagatg    6960
ctgtctgttc acgttggaac tgccatccac aaccaagcag ctctttgtca gtcagttgan    7020
anctattggc agtgtggaat ccagctcctc acacagttcc agantcagtc caaggtgggg    7080
aaangctccc tgcttgtggg tgtgtccttc ttacattccc tacataacat gatcctgtat    7140
```

```
aaaccatttc catttattat ggaactcttc tgggcactgc cctcctaatt agtgtttctc   7200
tgacatcacc aaacacagca tgggtatttc aggtttcaan atcattttat gtccttcaat   7260
cctaggggta gcttcaatta atgtcctgtg gcaanggant aaatgcctct catgtggaaa   7320
ttctctagtc caaagtgcna ntaattgtta ctganaagtg ttcacagtct tttgccataa   7380
gtgccagttt cccttccaca taagactatc agacagataa tttgtcccta ccaccactcc   7440
agcttctact atacaccatt gggcctgggc agtgctgttg gtccccattt agcatgtcca   7500
gttaatattg tcatgaaggg cagatttaca tgccttttgt tttacagtac tangtanggg   7560
aagtgtgtct ccagccagac atatccattc tcataaaaca tttaggtaaa ggggatataa   7620
cttctttacg taaagctcac ttaaacatcc taactttcat aattctatca acccttgcat   7680
ttttatgttc tccaatctaa ttgtatcctg aatcagggct ttaccaatag atcttgatac   7740
cacantacat ggagctccca taccaangan tcccaggaat ttatcttcac caccccgacc   7800 attttacccca cttgtntatg anaagccttt ggttcccnnc acaaacagaa aaatanatcc   7860
ttgcccattt gtcagtcatt atcttgantt aatcaatctg tctattgccc caagcaattg   7920
ttggtcactt ttcttgtaat ctctgccttc tggcttttta agtttccccg aatttacaga   7980
catcatatga cctttgtcca nagaatatag ctaggaaata tctganattg ctcccaccca   8040
ctaaagtaaa ccccattacc cagttaatta nctgaaagtc acactgttct atcgtntacc   8100
ttagtngaat ntttcctgtt aaantatntn gggaatgttg gcattccctc tcttaagttn   8160
agggtccaan tggatttnga tccttggagc acttcncaan atccctattg tttntgttgt   8220
catgtccatc nctctgactc taanaaaaat attgtattat atctatctat ctatctatct   8280
atctatctat ctatctatct atctatctat ctatatctat ctacctatgt acctacctac   8340
ctacctacct acctaccgtt tcctgttttc cagatataaa caaaccctag gcagcacatt   8400
aatttattaa ctttaccaga gtttgccata ctctcaagtc tcaatattgt agatgatttt   8460
ttatgaggct aaacatattt cattttgctt gtaccaaaat gaaaacaact ttcttatgtt   8520
acatgatgcc aggctatatc ctatgtaagg tcatgggtgg ggaatnttac tttaactggc   8580
actttattca gtgctacaag tttattaaga ngtgtttcag gcattccaac aaaaatttaa   8640
aatataactt tgtggagttg cnattgattt aattgcttta gagttgcttc agattcattt   8700
cttgaaaatt cttcccttct gattatgatt ttacctctga agaatgccac tcaagaattt   8760
atnattangc caggtgcagt ggcttaccct gtaatccaag cactttggga ggctggggtg   8820
ggtggatcac gaggtcagga gttcaagacc agcctggaca acatggcaaa accccatctt   8880
aaaaatacaa aaattagcca ggcttgctgg tgggcgcctg tactcccagc tactagggag   8940
gctgaggcag gagaattgct tgaacccggg aggcagaggt tgcagtgagc tgacatcacn   9000
ccattgcact ccancctggg tgacaaanca aggctctgtc tcnaaaaaaa aaaaaataga   9060
atttataatt aatagtcact ttaaacttac tggcatttat atgtttactt tgcagtgttg   9120
tgtgtgtgtg tagtcagcag ctttgcaaaa gaatttacta cagaaacagt acaaatgcaa   9180
tgtaaaaaaa ttagaaaata caaatatgca aaaattggaa atgacatttt catgacccan   9240
anatnaatac ttttaacatc ctanagtata tccttccana ttgtgttttt tttttctgt   9300 gcctgtacgt acacataaac ttttaaccta aatggcaaca tgccatatat acttcttttt   9360 tttttttga nanaaanttt cacncttgtt gcccaggctg gagtacaatg ttgcaatctt   9420
ggctcattgc aacctcttgc ctcccgggtt caagcaattc tcctgcctca gcctcccaag   9480
```

```
tagctgggat tacaggcatg tgccaccgcc actacgccca gctaattttt gcattttag    9540 tagagacggg gcttcaccat gttggccagg ctggtcttga actcctgacc tcgtgatcct    9600
cccccccccc ccacaaagtg ctgggattac aggcatgagc caccatgccc agatgtatag    9660 ttggttttt tgggggtttt ttttgaaaaa atcttgctct gtcacccagg ctggaatgca    9720
ttggcgcgat ctcagctcac tgcaacctct gcctcccaaa ttcaagcaat tctcatgcct    9780
cagcctcccg attagctggg actacaggcg tgcactacca cacctggcta attgttgtgt    9840
ttttagtaga cagggttt caccatgttg attaagctgg tctcaaactc ctgacttcag    9900
gtgagccacc tgccttggcc ttccaaagtg ctgggattac aggtatgagc cactgtgccc    9960
ggcccagata tactatttta taaactactt atttaggcaa tgatntccac cattttgttt   10020
cagtagattt cttcttcttt cttccttctt ttccttcct tctttttcaa ggttgttatg   10080
gttttctagt tttggtacag tgagaatgtt gttttttatat cttgtttgtt tttgcattca   10140
tatatgatag ttatataggg atagtaaaac aaatacatac ttttccatat ataaagggtc   10200
aaaggaaggc actgaatttt atttatgtat tttaacacgg agtntcactg ttgcccaggc   10260
tggattgcag cggcgcaatc tcggctcact gcaacctccg cantgggttc aagtgattct   10320
cctgccttat cctgccgatt aactgggatt actggcacat gccaccatct ccagctaatt   10380 ttttgtatttt taagtaaaga tgggggtttca ccatattggc caggctggtc tcaaactcct   10440
gacctcaagt gatccgccca ccttgacctc ccaaagttat gggattacag tcatgagcca   10500
ttgtgntcgg ccagaatgca ctgaatttta tgtgatcctt tttgtacaca ggaaactcct   10560
gtaaattatt agttttaaaa tagtaactat aattttttta acatccttat tttgggattt   10620
gaaattcttt tttttttatt tttgagacgg agtctcgctc cttcgcccag gctggagtgc   10680
agtggcgcta tctcggctca ctgcaagctc cgcctcctgg gttcatgccg ttctcctgcc   10740
tcagcctccc gagtagctgg gactacaggc gcccgccacc gcacccagct aattttttgt   10800 attttagta gagacggggt ttcactgttt tagccaggat ggtnttgatn tcctgacntc   10860
angatccgcc cgcntcagct tcccaaagtg ctgggatnac aggcgtgagc caccgtgccc   10920
ggcagggatt tgaaattctt ataaggaagt cttgctaaat caaggtggaa atcaggtgtt   10980
accaaaatta ggctagcttt gtagtaaata tntgtttttnt tagcaggaaa tgaatcaaat   11040
gtctttcaga agtcagattg cttccattgt gtctatcatt ggggatatta ccataaagca   11100
cagaaaattg aggtgctttg taattacagt gggcttcagg gtatacattt cattgcattt   11160
tagcctttat aagtattgtt tttgaaggtt ttacatgtta tcttaagcac atgtacgtgc   11220
ctttaatggc acatagtaaa ccagttttaa taaaagttga ccacgtccta atagtaaagt   11280
tacaatagca ttttaaatct tactagtgat ttaatagttt caccatttaa catttgtagg   11340
gccaggaaaa gctgcttata agactcacgg gcacagagta agtatattca ctttgagact   11400
gtgtgatata tgtatgcata gggaggcaaa ggacccaaat gctgaccttt taaaaatgac   11460
ttctcttctt tttttganat ggantctcac tctgtcactc aggctggant gcaatggtgt   11520
gatattggct cacagcagcc tccaccccccc aaattcaant gattctcttg tttcagcctc   11580
ccaantacct gggattacag gcttgcatca ccacacctgg ctaattttg tatttttagt   11640 aaaaatgggg tttcaccatg ttggccagnc tggtcttgaa ctctattaan gtgatccacc   11700
tgcctcagcc tcccaaantg ttgggattac aagancganc cacagcgcct ggcctaaaaa   11760
taattttctt tatatnaact ttttctatt antttcttat tgtggcctct taaaatncta   11820
ctgtaaaaaa attttatata tatatgtgtg tgtgtgtgtg tgtaataaat atgtgtgttt   11880
```

```
cctcaagtga ttttaggcag aatgtgtcac tgcccttcct gtgtaaaata actcttaaaa    11940
atcatacagc tcttcatgtt acgtgttgac atagtttaca gcaatcctac ttgattagct    12000
tttttatatg gaaaacataa tcatactgtg tgtagccaat tttaagattg tgttattcaa    12060
gantcttata ttgccatgta aataccatct caaaatgtgc cctgttgtga gataaagaaa    12120
aacttaagag atttattcta ttaagctata gcttttatc tagaaaaatg gcaaatgagt     12180
agaatttcca tatgcaaatt tctattaaat aaagatttaa agcatgtttc ctggaacatt    12240
ttacttatag acaggaaatg tcttgtgaag gtattgtgag cacactgctt tctgatcagt    12300
aaaattnggg aattaaaata ttttcctttt aagattatgg tgagaattaa aatatatatt    12360
tgcaaaagaa ttggcaaatg cagatattca ataaatgtta gntcccctcc cagacaagct    12420
tatataaatg tgtgtgctcc gtaaatgaaa ttcaaagttt aaagtgtatt tttagaaaac    12480
agtctactta gtgagccatc tggggcttat atggctcttt ctataacagt tgtttccttc    12540
caccactatc agtcagtggg gtnanngaat aataaaattg tttgtnagcc atgaaacana    12600
agntttnatt nagccataaa caaantagng tggcaaattg aattgntaag taacttttcc    12660
agttttgtta ataacatant ctgttattta anacatcccc accccnttct gtttcagagt    12720
ggaagctcaa aatgaaatgg ggcagcatat tcattgttat gttgcagctc ttgctgctca    12780 tacaacttt ctggaacaac ccaagagctt tcgcccttcc cagtggataa aagaacacag      12840
tgaaagacag cctcttaaca gaaatagcct tcgtcgccaa aatcttacca gggattgcca    12900
ccctcggcaa gtcaagcaca atggctgggt tgttcatcag ccctgcccgc gtcagtacaa    12960
ttactaatag tttcaagttt tgttggttgg tttctcttgg tttgtgctaa catgtatgga    13020
tgtgtgtata tgtacagtga aaatgttgtc tctttacaac caattgataa ccaatcacat    13080
agttttatca gtgtatttag acactatctt gaaaatcaga tttatatgct gtgtatcaca    13140
taatgccttg cctttaacat ttacttttt tgtacactt tcagattat ttctggaaac       13200 atatcaatat aattacagtg tttgggggtg tcttaaaata tattaggtta tacattagtc    13260
agcattttaa agacatttct tcccaagtac gagaataggc atctttcatt ttcattttat    13320
tttgtattac ttaatctttt aagcaagcaa aaatttattc tcagggtcag ctgtacactt    13380
tattgaccag tacttgataa tctctctgta tatgatgaat acatttttat acactaacat    13440
tagcattaac aggtgatagt tgccatggat ataatggaat tatggctgga cttctttg      13500 aaagaaaact tgatgtattc tgtgtgtatg gttttccc agattagtca tacagttcat       13560
ttggaattca ggtacattaa gctttagtga agagtgcatg cagtaattcc aatgtgactg    13620
catgacgtgg tacagacatt acaggtgttg tagacagagg cacttgtctc gtgcagaggg    13680
attaaattag acctgtgaga ttatatttgg aaaaattcat gtctgtaact aacccattag    13740
tgcagtattt aatttgttac tattccttcc cgccaattct gtccactcct cacctcgcat    13800
cagctataaa tttggaaata cttgtccagg cactcaagtg acttcatatt tctctctgcc    13860
catgggaaaa gagataggct ttatatttcc acagantgaa aaatcctctg tcatggagcc    13920
tgtcctgcca agtggcaaga atgtggggac tgtctggtga tgatgtcttt catggcatct    13980
gagtgaagaa tgacaggttg gctcaacttt ttcttttt ttttttaatt gccttgtatt     14040
gtaagtattc ttccctgcag tccaagtgac ttttcatttt ttgtttaac ttcaggcaaa     14100 atctttaacc actctggcct ctgtttcccc caccaacggg gagcagtgac atttacctcc    14160
ctcacagagt cactgtgagg attctatact gatttgaagt ggagctgttc agaactgaac    14220
```

```
cttgtaggaa attccaaggg cctttctact gaatctggtg atggggtggg gccgtggcac    14280
tttctctgcc acagctgttc ttcacagtgt tggtgctaat gaggccaggg tgcagggttc    14340
gattcacacg taggccagtt aacttagaga aaatctattt ccttacctct agccagtcac    14400
ttccttttc cgcagttgtg atgggttttg ctgagccatc cactctgact gatttcctct    14460
gaagtaaaca tatttacaat ccaaagcaat tctactgaca gaagtgttgc cttcataatc    14520
aaacagcttg tttttccatc tcctctgcaa ccctaattaa atgagtacag gtctacaaaa    14580
tgttttcaag gagaaaagca gcatatcctt aagtgaagta ttatatttt caataaccct    14640
gtagtggctt gatgcaggga accctggggg actttcagcg aagagctgtg ctcttttctg    14700
actagattag agcgtttgga gtggaagacg tcaaatgtgt agtgagatgg aggttttaca    14760
ttgttcttct actggctgtg atgaagtgcc agaatgtctc tttagaacaa gagttagatt    14820
ccccctttct ccttattgcc ccttccgttt tgacttcccc tttatttatt tgctgtctaa    14880
ttaggggcca agtctgtaaa gttttgtcaa agtgagttag aagttgtttt tcttactat    14940
ttgtgtttac cagagttggg agataagata gtttccatga aggtgtgtat gttttatacg    15000
atgtttgtta tagggccatg cattggtaac ttgaaaataa gacagcttaa tgtcttcagg    15060
atgtaatcag acagcttaat gtcttcaggg atgtaaaact ctgactacac ggcgtctctt    15120
tttcatacat tgcatgtaag ttgttagtac ctcacaagct acagaagttc agccatgaga    15180
ttttgtttgg caacatgaac agatttgtgt ataactgcaa tggcctttt tccagatttc    15240
cttattgact ttttgtttgc cttacctggg gctagttttt tatgctttgt acctagaaaa    15300
caaaaaatta cattcgttgg gctttttttc aaggttggga ttaccacacc acctggaata    15360
tcatactgtg gtttctgcct aaaattggca catgtaagta ttgaagaaaa tggttatata    15420
attcagttga aactcttggt tattagatgt taggcatctc ctgtatgtaa gacacaaggc    15480
caaccacaac acagaacgat gttgacctgt taagtattct ctgaaacatg gccaaaatgc    15540
atttatgag cttttttttt ttgctattgt aaatattagt ggtttacaat gcgctttaaa    15600
catatttctt taaatgcaa gcagtgagaa ataagacctc tctgaattag tagctctaaa    15660
ctgttaacat agaatgttac ttggaaaaag tctggaatat gtggtgtaca caagcagtgc    15720
ttcgtgaatg agtttcttag ctttttatagt gcgccatgtt tctcaaagtt tgttttttgtt    15780
gacaaaacat tttataatat atatcttatg tttatttttt ttctcaacta attgtgtact    15840
gcactgtaag gtgaaaatta gccatccatt atttatcttc tgtggcaatg catttatatg    15900
gttgattggg tggggaattt tttgcagaaa gatgcaaagt gatgggtttt cgacttccta    15960
tcgcagggag cttttaagaa atattaattt cctatacatt tttccaatcc ccatgcaaac    16020
tgttcctgtt tacataccctt ctctgttgta tcagtacttt gagtgagaag acagtttatt    16080
taaaacttga gcaggctgtt cagcattttt tctgcttctg aaatctgtat agtacactgg    16140
tttgtaatca ttatgtcttc attgaaatcc ttgctacttc tcttcctcct caatgaaata    16200
cattatatat tatctttatg tactcttaag aaaaacgagc aaggaagagt atcttcatta    16260
ttctcatttt ctctgagttg gaaacaaaaa catgaaggac tccaactaga agacagatat    16320
ttacatttaa atagattagt gggaaaactt taagagtttc cacatattag ttttcatttt    16380
ttgagtcaag agactgctcc ttgtactggg agacactagt agtatatgtt tgtaatgtta    16440
ctttaaaatt atcttttttat tttataaggc ccataaatac tggttaaact ctgttaaaag    16500
tgggccttct atcttggatg gtttcactgc catcagccat gctgatatat tagaaatggc    16560
atccctatct acttacttta atgcttaaaa ttatacataa aatgctttat ttagaaaacc    16620
```

```
tacatgatac agtggtgtca gccttgccat gtatcagttt cacttgaaat ttgagaccaa    16680
ttaaatttca actgtttagg gtggagaaag aggtactgga aaacatgcag atgaggatat    16740
cttttatgtg caacagtatc ctttgcatgg gaggagagtg actcttgaaa ggcaggcagc    16800
ttaagtggac aatgttttgt atatagttga gaattttacg acacttttaa aaattgtgta    16860
attgttaaat gtccagtttt gctctgtttt gcctgaagtt ttagtatttg ttttctaggt    16920
ggacctctga aaaccaaacc agtacctggg gaggttagat gtgtgtttca ggcttggagt    16980
gtatgagtgg ttttgcttgt attttcctcc agagattttg aactttaata attgcgtgtg    17040 tgttttttt ttttttaagt ggctttgttt ttttttctca agtaaaattg tgaacatatt    17100
tcctttatag gggcagggca tgagttaggg agactgaaga gtattgtaga ctgtacatgt    17160
gccttcttaa tgtgtttctc gacacatttt ttttcagtaa cttgaaaatt caaaagggac    17220
atttggttag gttactgtac atcaatctat gcataaatgg cagcttgttt tcttgagcca    17280
cggtctaaat tttgttttta tagaaatttt ttatactgat tggttcatag atggtcagtt    17340
ttgtacacag actgaacaat acagcacttt gccaaaaatg agtgtagcat tgtttaaaca    17400
ttgtgtgtta acacctgttc tttgtaattg ggttgtggtg cattttgcac tacctggagt    17460
tacagttttc aatctgtcag taaataaagt gtcctttaac ttcaaaaaaa aaaaaaaa    17518
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 6
ttgtgggtga agtcagttct t                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
gagcttccac tctgggact                                                 19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:p53-binding
      sequence in intron2

<400> SEQUENCE: 8
gaacttgggg gaacatgttt                                                20

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence
```

```
<400> SEQUENCE: 9
cgccgagctc cctgcaatac tcacactgc                                    29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
cagtacgcgt cctccataag accccaata                                    29

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized sequence

<400> SEQUENCE: 11
cgaacttggg ggaacatgtt ta                                           22

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized sequence

<400> SEQUENCE: 12
cgcgtaaaca tgttccccca agttcgagct                                   30

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:an
      artificially synthesized sequence

<400> SEQUENCE: 13
cgaacttggg ggaacatgtt tgaacttggg ggaacatgtt ta                     42

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence:an
      artificially synthesized sequence

<400> SEQUENCE: 14
cgcgtaaaca tgttccccca agttcaaaca tgttccccca agttcgagct             50

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized antisense oligonucleotide sequence

<400> SEQUENCE: 15
```

```
tggaacattg ttaagg                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized antisense oligonucleotide sequence

<400> SEQUENCE: 16
tcagcctctg gaacat                                                    16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized sense oligonucleotide sequence

<400> SEQUENCE: 17
ccttaacaat gttcca                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:an
      artificially synthesized sense oligonucleotide sequence

<400> SEQUENCE: 18
atgttccaga ggctga                                                    16
```